(12) United States Patent
Czerwiec et al.

(10) Patent No.: US 10,412,089 B2
(45) Date of Patent: Sep. 10, 2019

(54) DEVICE BASED RISK MANAGEMENT OF A THERAPEUTIC

(71) Applicant: Otsuka Pharmaceutical Co., Ltd., Tokyo (JP)

(72) Inventors: Frank S. Czerwiec, Potomac, MD (US); Amy Freedman, Yardley, PA (US); Keith Friend, Gladstone, NJ (US); Elaine A. O'Hara, Malvern, PA (US); Craig Ostroff, East Windsor, NJ (US); Marcelo De Freitas Santoro, Chester Springs, PA (US); Charles Shiner, Collegeville, PA (US); Takeshi Watanabe, Tokyo (JP); Miho Yamamoto, Tokyo (JP); Christopher A. Zimmer, Washington, DC (US)

(73) Assignee: OTSUKA PHARMACEUTICAL CO., LTD., Tokyo (JP)

(*) Notice: Subject to any disclaimer, the term of this patent is extended or adjusted under 35 U.S.C. 154(b) by 302 days.

(21) Appl. No.: 15/219,866

(22) Filed: Jul. 26, 2016

(65) Prior Publication Data
US 2016/0335411 A1 Nov. 17, 2016

Related U.S. Application Data

(63) Continuation of application No. PCT/US2015/013491, filed on Jan. 29, 2015.
(Continued)

(51) Int. Cl.
*G06Q 10/10* (2012.01)
*G06Q 10/06* (2012.01)
(Continued)

(52) U.S. Cl.
CPC ............ *H04L 63/10* (2013.01); *G06Q 10/10* (2013.01); *G06Q 10/101* (2013.01);
(Continued)

(58) Field of Classification Search
CPC .. G06Q 10/101; G06Q 10/018; G06Q 10/105; G06Q 50/205; G06Q 50/265;
(Continued)

(56) References Cited

U.S. PATENT DOCUMENTS 5,580,794 A  12/1996  Allen
5,629,327 A   5/1997  D'Amato
(Continued)

OTHER PUBLICATIONS

International Search Report for International Application No. PCT/US2015/013491, dated Jun. 15, 2015.
(Continued)

*Primary Examiner* — Jonathan P Ouellette
(74) *Attorney, Agent, or Firm* — Cooley LLP

(57) ABSTRACT

A risk management system (RMS) device includes a RMS database and a RMS processor. The RMS processor includes a prescriber module to receive a request to enroll a patient in a RMS program of a therapeutic agent associated with multiple indications. The request includes a specification of at least one indication, and a confirmation of a diagnostic test conducted on the patient. The RMS processor also includes a patient module configured to generate a patient profile. The RMS processor also includes a database module configured to store the patient profile in the RMS database. The RMS processor also includes an authorization module configured to generate an authorization code indicating whether the patient is authorized to receive the therapeutic agent. The RMS processor also includes a communication module configured to transmit the authorization code to a pharmacy or a prescriber.

16 Claims, 14 Drawing Sheets

Related U.S. Application Data

(60) Provisional application No. 61/932,985, filed on Jan. 29, 2014.

(51) Int. Cl.

| | | |
|---|---|---|
| *G06Q 10/08* | (2012.01) | |
| *H04L 29/06* | (2006.01) | |
| *G06Q 50/26* | (2012.01) | |
| *G06Q 50/24* | (2012.01) | |
| *G16H 10/60* | (2018.01) | |
| *G16H 50/30* | (2018.01) | |
| *G16H 50/20* | (2018.01) | |

(52) U.S. Cl.
CPC ........... *G06Q 10/105* (2013.01); *G06Q 50/24* (2013.01); *G06Q 50/265* (2013.01); *G16H 10/60* (2018.01); *G16H 50/20* (2018.01); *G16H 50/30* (2018.01)

(58) Field of Classification Search
CPC ........ G06Q 50/24; G06Q 10/10; H04L 63/10; G16H 10/60; G16H 50/30; G16H 50/20
USPC ......... 705/300, 317, 320, 325, 326, 1.1–912
See application file for complete search history.

(56) References Cited

U.S. PATENT DOCUMENTS

| | | | |
|---|---|---|---|
| 5,635,517 A | 6/1997 | Muller et al. | |
| 6,045,501 A | 4/2000 | Elsayed et al. | |
| 6,067,524 A | 5/2000 | Byerly et al. | |
| 6,140,346 A | 10/2000 | Andrulis, Jr. et al. | |
| 6,235,756 B1 | 5/2001 | D'Amato | |
| 6,281,230 B1 | 8/2001 | Muller et al. | |
| 6,315,720 B1 | 11/2001 | Williams et al. | |
| 6,317,719 B1 | 11/2001 | Schrier et al. | |
| 6,397,190 B1 | 5/2002 | Goetz | |
| 6,555,554 B2 | 4/2003 | Muller et al. | |
| 6,561,976 B2 | 5/2003 | Elsayed et al. | |
| 6,561,977 B2 | 5/2003 | Williams et al. | |
| 6,639,515 B2 | 10/2003 | Hougaard | |
| 6,694,298 B1 | 2/2004 | Teagarden et al. | |
| 6,755,784 B2 | 6/2004 | Williams et al. | |
| 6,767,326 B2 | 7/2004 | Elsayed et al. | |
| 6,869,399 B2 | 3/2005 | Williams et al. | |
| 6,908,432 B2 | 6/2005 | Elsayed et al. | |
| 7,059,526 B1 | 6/2006 | Sullivan et al. | |
| 7,115,277 B2 | 10/2006 | Firestone et al. | |
| 7,119,106 B2 | 10/2006 | Muller et al. | |
| 7,141,018 B2 | 11/2006 | Williams et al. | |
| 7,189,740 B2 | 3/2007 | Zeldis | |
| 7,230,012 B2 | 6/2007 | D'Angio et al. | |
| 7,267,278 B2 | 9/2007 | Lammle | |
| 7,382,255 B2 | 6/2008 | Chung | |
| 7,435,745 B2 | 10/2008 | D'Amato | |
| 7,461,006 B2 | 12/2008 | Gogolak | |
| 7,465,800 B2 | 12/2008 | Jaworsky et al. | |
| 7,668,730 B2 | 2/2010 | Reardan et al. | |
| 7,744,540 B2 | 6/2010 | Rao et al. | |
| 7,765,106 B2 | 7/2010 | Reardan et al. | |
| 7,765,107 B2 | 7/2010 | Reardan et al. | |
| 7,765,110 B1 | 7/2010 | Koneru | |
| 7,797,171 B2 | 9/2010 | Reardan et al. | |
| 7,831,444 B2 | 11/2010 | Brown et al. | |
| 7,874,984 B2 | 1/2011 | Elsayed et al. | |
| 7,885,824 B1 | 2/2011 | Koneru | |
| 7,885,827 B1 | 2/2011 | Koneru | |
| 7,895,059 B2 | 2/2011 | Reardan et al. | |
| 7,959,566 B2 | 6/2011 | Williams et al. | |
| 7,962,349 B2 | 6/2011 | Silverbrook et al. | |
| 7,968,569 B2 | 6/2011 | Zeldis | |
| 7,977,357 B2 | 7/2011 | Jaworsky et al. | |
| 8,086,470 B2 | 12/2011 | Siegel | |
| 8,099,244 B2 | 1/2012 | Niggebrugge | |
| 8,099,298 B2 | 1/2012 | Coleman et al. | |
| 8,112,290 B2 | 2/2012 | Maurer et al. | |
| 8,193,219 B2 | 6/2012 | Jaworsky et al. | |
| 8,204,763 B2 | 6/2012 | Elsayed et al. | |
| 8,275,552 B1 | 9/2012 | Trotti, III | |
| 8,288,415 B2 | 10/2012 | Muller et al. | |
| 8,315,810 B2 | 11/2012 | Von Busch et al. | |
| 8,315,886 B2 | 11/2012 | Williams et al. | |
| 8,370,171 B2 | 2/2013 | Stephenson | |
| 8,386,274 B1* | 2/2013 | Pinsonneault | G06Q 50/24 705/2 |
| 8,392,219 B1 | 3/2013 | Pinsonneault et al. | |
| 8,392,220 B2 | 3/2013 | Knowlton et al. | |
| 8,404,717 B2 | 3/2013 | Zeldis | |
| 8,431,598 B2 | 4/2013 | Jaworsky et al. | |
| 8,452,815 B2 | 5/2013 | Smith et al. | |
| 8,457,988 B1 | 6/2013 | Reardan et al. | |
| 8,457,989 B2 | 6/2013 | Gedeon et al. | |
| 8,473,315 B1 | 6/2013 | Lucchino | |
| 8,478,604 B2 | 7/2013 | Henderson et al. | |
| 8,484,085 B2 | 7/2013 | Wennberg | |
| 8,489,417 B2 | 7/2013 | Hoffman et al. | |
| 8,509,884 B2 | 8/2013 | Snyder | |
| 8,515,780 B2 | 8/2013 | Soto et al. | |
| 8,515,932 B2 | 8/2013 | Classen | |
| 8,543,422 B2 | 9/2013 | Maman et al. | |
| 8,589,188 B2 | 11/2013 | Elsayed et al. | |
| 8,626,531 B2 | 1/2014 | Williams et al. | |
| 2003/0060688 A1* | 3/2003 | Ciarniello | G06Q 40/08 600/300 |
| 2004/0078231 A1 | 4/2004 | Wilkes et al. | |
| 2004/0117126 A1* | 6/2004 | Fetterman | G06F 19/3456 702/19 |
| 2004/0128165 A1 | 7/2004 | Block et al. | |
| 2005/0149362 A1 | 7/2005 | Peterson et al. | |
| 2007/0093497 A1 | 4/2007 | Walsh | |
| 2007/0162309 A1* | 7/2007 | Denny | G06F 19/3456 705/2 |
| 2007/0219825 A1* | 9/2007 | Maetzold | G06Q 50/22 705/2 |
| 2008/0126117 A1* | 5/2008 | Miller | G06Q 10/10 705/2 |
| 2008/0154514 A1 | 6/2008 | Magness et al. | |
| 2008/0201173 A1 | 8/2008 | Takehara et al. | |
| 2008/0215362 A1 | 9/2008 | Powell et al. | |
| 2009/0198518 A1 | 8/2009 | McKenzie et al. | |
| 2010/0088120 A1 | 4/2010 | Gonzalvo | |
| 2011/0145018 A1 | 6/2011 | Fotsch et al. | |
| 2011/0166876 A1 | 7/2011 | Chapman et al. | |
| 2011/0184747 A1* | 7/2011 | Bozic | G06Q 50/22 705/2 |
| 2011/0282690 A1* | 11/2011 | Patel | G06Q 30/0603 705/3 |
| 2011/0297563 A1 | 12/2011 | Scarazzini | |
| 2012/0035958 A1 | 2/2012 | Rhine-Pallas et al. | |
| 2012/0065514 A1 | 3/2012 | Naghavi et al. | |
| 2012/0065999 A1 | 3/2012 | Takatoku et al. | |
| 2012/0316894 A1 | 12/2012 | Williams et al. | |
| 2013/0101972 A1 | 4/2013 | Scarazzini | |
| 2013/0197934 A1 | 8/2013 | Trifunov | |
| 2014/0249832 A1* | 9/2014 | Link | G06Q 50/22 705/2 |
| 2014/0288944 A1 | 9/2014 | Miller et al. | |
| 2014/0316797 A1* | 10/2014 | Biernacki | G06F 19/3456 705/2 |

OTHER PUBLICATIONS

Law Firm of Pepper Hamilton LLP, "Pharmaceutical Patent Life Extension Strategies: Are REMS Programs Next?" Mar. 2012. www.pepperlaw.com/publication_article.aspx?ArticleKey=2335.

Sandra Wells, "The Impact of REMS on Generic Drug Approvals and Drug Competition" the RP, Report, May 2012, vol. 8, No. 6.

Kurt R. Karst, "FDA Largely Denies Citizen Petition on Single, Shared REMS System, But Outlines Agency Standards and Processes", FDA Law Blog, Hyman, Phelps & McNamara, P.C., Oct. 21, 2013.

(56) References Cited

OTHER PUBLICATIONS

Toliver, K. A. et al., "Summary Minutes of the Drug Safety and Risk Management Advisory Committee Meeting," Meeting of the Cardiovascular and Renal Drugs Advisory Committee, Silver Spring, Maryland, Aug. 5, 2013, 6 pages.

Otsuka Pharmaceutical Development & Commercialization, Inc., "Delaying Progression of Renal Complications of Autosomal Dominant Polycystic Kidney Disease by Tolvaptan Inhibition of Arginine Vasopressin," Tolvaptan (OPC-41061), NDA 204441, Briefing Document for Aug. 5, 2013 Advisory Committee Meeting of the Cardiovascular and Renal Drugs Division of the US Food and Drug Administration, Rockville, Maryland, Jul. 3, 2013, 224 pages.

Otsuka Pharmaceutical Development & Commercialization, Inc., "Delaying Progression of Renal Complications of Autosomal Dominant Polycystic Kidney Disease by Tolvaptan Inhibition of Arginine Vasopressin," Tolvaptan (OPC-41061), NDA 204441, Errata to Briefing Document for Aug. 5, 2013 Advisory Committee Meeting of the Cardiovascular and Renal Drugs Division of the US Food and Drug Administration, Rockville, Maryland, Jul. 24, 2013, 17 pages.

Lawrence, J. et al., "NDA 204441 Tolvaptan Clinical and Statistical Findings," Cardiovascular and Renal Drugs Advisory Committee Meeting, Aug. 5, 2013, U.S. Food and Drug Administration, 48 pages.

Otsuka Pharmaceutical Development & Commercialization, Inc., "Tolvaptan: Slowing Progression of Autosomal Dominant Polycystic Kidney Disease (ADPDS)," Cardiovascular and Renal Drugs Advisory Committee Meeting, Aug. 5, 2013, 135 pages.

Reckitt Benckiser Pharmaceuticals Inc., "SUBOXONE® (buprenorphine and naloxone) sublingual tablet CIII Buprenorphine (opioid partial agonist-antagonist) Naloxone (opioid antagonist)," NDA 20-733, Richmond, Virginia, Dec. 2011, 57 pages.

Gilead Sciences, Inc., "TRUVADA O (emtricitabine/tenofovir disoproxil fumarate) Nucleoside/Nucleotide Analog Human Immunodeficiency Virus-1 Reverse Transcriptase Inhibitors," Supplemental NDA 21-752, Foster City, California, Jul. 16, 2012, 106 pages.

Vivus, Inc., "QSYMIA (phentermine and topiramate extended-release) Capsules [Category: anorectic and antiepileptic]," NDA 22580, Mountain View, California, Jul. 2012, 163 pages.

\* cited by examiner

DEVICE BASED RISK MANAGEMENT OF A THERAPEUTIC

PRIORITY TO RELATED APPLICATION

This application claims priority to and is a continuation of PCT Application No. PCT/US2015/013491 titled "DEVICE-BASED RISK MANAGEMENT OF A THERAPEUTIC" filed Jan. 29, 2015, which claims priority to U.S. provisional application No. 61/932,985 titled "SYSTEMS, APPARATUSES, AND METHODS FOR RISK MANAGEMENT OF A THERAPEUTIC" filed Jan. 29, 2014, the disclosures of each of which are incorporated herein by reference in their entirety.

BACKGROUND

Therapeutics such as medications have the potential to considerably improve the health and well-being of patients, but medication use is not without risk, particularly in unmonitored, out-patient settings. Despite increasing risk mitigation activities and risk communications from regulatory bodies such as the Food and Drug Administration (FDA), several medications with known, preventable risks have been withdrawn from the market or placed on restricted distribution because of a lack of appropriate patient monitoring. In other cases, medications continue to be inappropriately prescribed to patients who have contraindications to a medication's use that manifest once the patient starts using the medication.

Thus, there exists a need for effective device-based risk management of therapeutics having known contraindications and/or side effects.

SUMMARY

Figure 1:
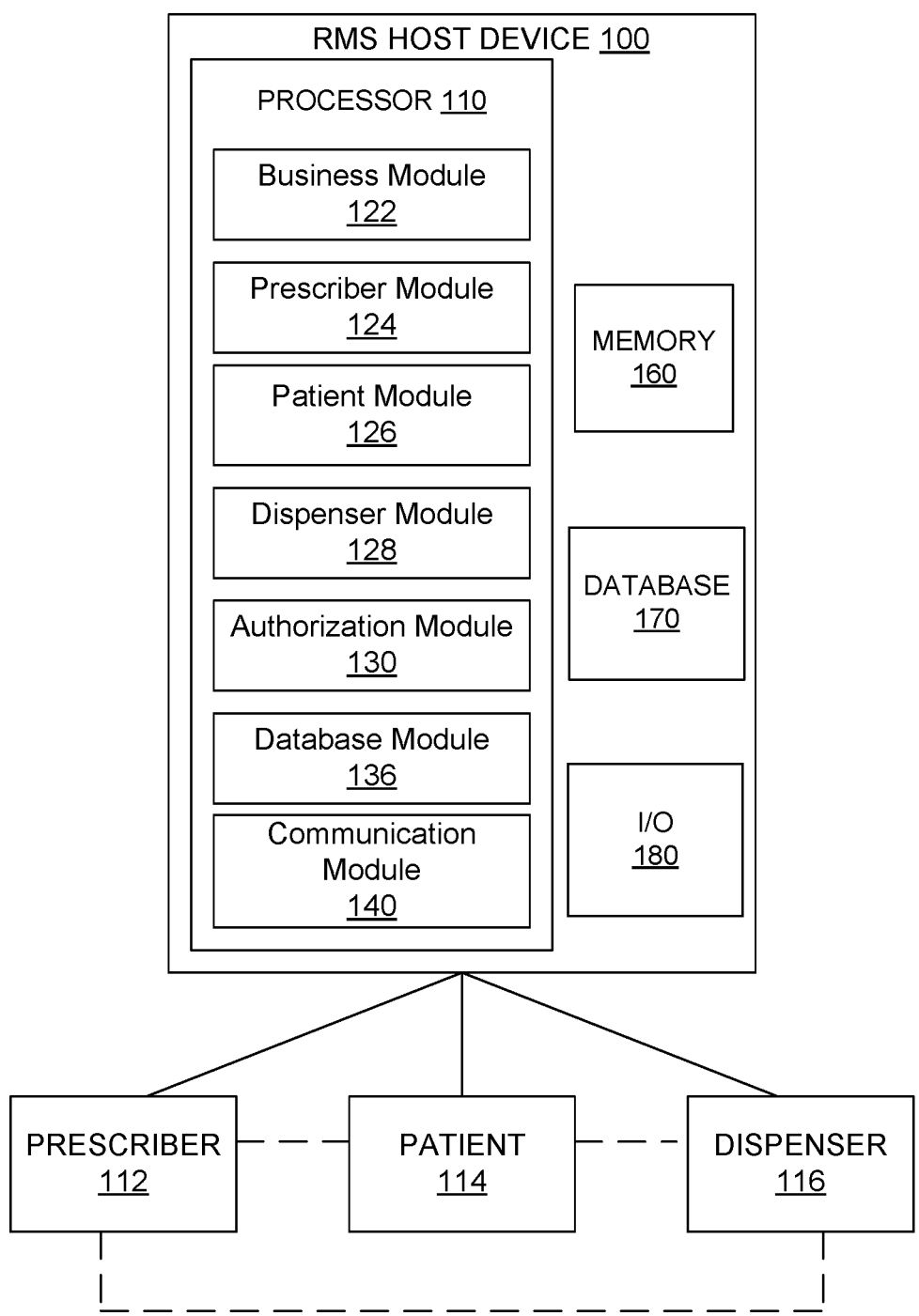
FIG. 1 is a schematic illustration of a system including a RMS host device, according to an embodiment.

A risk management system (RMS) device includes a RMS database and a RMS processor. The RMS processor includes a prescriber module to receive a request to enroll a patient in a RMS program of a therapeutic agent associated with multiple indications. The request includes a specification of at least one indication, and a confirmation of a diagnostic test conducted on the patient. The RMS processor also includes a patient module configured to generate a patient profile. The RMS processor also includes a database module configured to store the patient profile in the RMS database. The RMS processor also includes an authorization module configured to generate an authorization code indicating whether the patient is authorized to receive the therapeutic agent. The RMS processor also includes a communication module configured to transmit the authorization code to a pharmacy or a prescriber.

DETAILED DESCRIPTION

Systems, devices and methods are described herein that enable management of risk of use of one or more therapeutic agents, such as prescription drugs (i.e., the restricted items) and potential side effects (risk) associated therewith. Aspects of the disclosure enable various entities involved in risk management, such as drug manufacturers, prescribers (e.g., medical professionals), patients, and dispensing entities (e.g., a hospital, an out-patient pharmacy, and/or the like) to interact in a manner that permits safe and informed use of a restricted drug/therapeutic agent, while mitigating known and unknown safety risks associated with the therapeutic agent.

In some embodiments, a risk management system (RMS) device includes a RMS database and a RMS processor. The term "RMS" or "risk management system" can represent any system that implements a management and/or distribution strategy for a therapeutic, such as a drug and/or a biological product, and can encompass scenarios in which such systems are mandated and/or desired by an entity in the supply/distribution chain (e.g., a manufacturer) of the therapeutic and/or a regulatory body (e.g., the United States' Food and Drug Administration (FDA)). For example, one such RMS can be used to implement a Risk Evaluation and Mitigation Strategy (REMS) that can be required if the FDA determines that a REMS is necessary to ensure the benefits of the therapeutic outweigh its risks. As another example, an RMS can encompass the risk management practices required by the European Medicines Agency relating to the post authorization follow-up of efficacy and adverse reactions for advanced therapy medicinal products. As yet another example, an RMS can encompass risk management guidelines of the Japanese Ministry of Health, Labor, and Welfare (MHLW)/Pharmaceutical and Medical Devices Agency (PMDA). In other embodiments, a RMS device can be initiated and/or implemented without being required by a regulatory body (e.g., by a manufacturer and/or distributor on a voluntary basis to mitigate risk).

The RMS processor includes a prescriber module configured to receive, via a communication network and from a compute device associated with a prescriber, a request to enroll a patient in a RMS program of a therapeutic agent associated with multiple indications. The request includes a specification of at least one indication, and a confirmation of a diagnostic test conducted on the patient. The diagnostic test is associated with the therapeutic agent and associated with the indication. The RMS processor also includes a patient module in communication with the prescriber module. The patient module is configured to generate in response to the request a patient profile by identifying a predetermined enrollment period based on the indication. The predetermined enrollment period can have a first duration when the indication is a first indication. The predetermined enrollment period can have a second duration different from the first duration when the indication is a second indication. The RMS processor also includes a database module in communication with the RMS database. The database module is configured to store the patient profile in the RMS database. The RMS processor also includes an authorization module configured to, based on the predetermined enrollment period, generate an authorization code indicating whether the patient is authorized to receive the therapeutic agent. The RMS processor also includes a communication module configured to transmit via the communication network the authorization code to at least one of a compute device associated with a pharmacy or the compute device associated with a prescriber.

In some embodiments, a RMS device includes a RMS database storing dispenser profiles, patient profiles, and prescriber profiles. The RMS device also includes a RMS processor. The RMS processor can include a dispenser module configured to receive, for a therapeutic agent associated with at least one indication, a request from a compute device associated with a pharmacy to dispense a first quantity of the therapeutic agent to a patient. The RMS database can include a dispenser profile for the pharmacy and the RMS database can include a patient profile for the patient. The RMS processor can also include a prescriber module configured to receive a confirmation of a successful diagnostic test of the patient from a compute device associated with a prescriber. The RMS database can include a prescriber profile for the prescriber. The RMS processor can also includes an authorization module configured to generate a first authorization code if the confirmation of the successful diagnostic test of the patient was received within a first predetermined time period. The authorization module can be further configured to generate a second authorization code if at least one of the following is true: (1) the confirmation of the successful diagnostic test of the patient is not received within the first predetermined time period, and the request from the compute device associated with the pharmacy is received within a second predetermined time period; or (2) a request is received from the compute device associated with the prescriber to dispense a second quantity of the therapeutic agent to the patient and different from the first quantity. The RMS processor can also include a communication module for transmitting the first authorization code or the second authorization code to the compute device associated with the pharmacy.

Aspects of the systems, devices, and methods described herein are further operable to ensure that prescribers are certified to prescribe the therapeutic agent via testing. In some embodiments, a method includes receiving, at a host device of a RMS system for a therapeutic agent associated with at least one indication, from a prescriber, a request to enroll the prescriber in the RMS. The method further includes providing, to the prescriber, educational material associated with the RMS and associated with the therapeutic agent. The method additionally includes providing, to the prescriber, access to a test relating to the educational material, and receiving, at the host device, an identifier of a performance of the prescriber on the test. The method also includes enrolling, at the host device, the prescriber in the RMS if the performance of the prescriber meets a performance criterion for the test.

Aspects of the systems, devices, and methods described herein are further operable to ensure that dispensers such as pharmacies are certified to dispense the therapeutic agent via testing. In some embodiments, a method includes receiving, at a host device of the RMS for a therapeutic agent associated with at least one indication, from a pharmacy, a request to enroll the pharmacy in the RMS. The method also includes providing, to a pharmacist associated with the pharmacy, educational material associated with the RMS and with the therapeutic agent, and further includes providing, to the pharmacist, access to a test relating to the educational material. An identifier of a performance of the pharmacist on the test can be received at the host device, and the pharmacy can be enrolled at the host device in the RMS if the performance of the pharmacist meets a performance criterion for the test.

Aspects of the systems, devices, and methods described herein are further operable to ensure that the patient receives the therapeutic agent and/or a refill of the therapeutic agent upon confirmation of the patient undergoing a diagnostic test required to receive the therapeutic agent and/or a refill of the therapeutic agent. In some embodiments, a method includes receiving, at a host device of the RMS for a therapeutic agent associated with at least one indication, a confirmation of a diagnostic test of a patient enrolled in the RMS by a prescriber enrolled with the RMS. The method also includes, based on the receipt of the confirmation by the prescriber, generating an authorization code indicating whether a pharmacy enrolled in the RMS is authorized to dispense the therapeutic agent to the patient. A request to dispense the therapeutic agent to the patient is received at the host device and from a compute device associated with the pharmacy. The authorization code can be provided to the compute device associated with the pharmacy.

Aspects of the systems, devices, and methods described herein are further operable to ensure that a patient can still avail of the therapeutic agent, albeit to a limited extent and/or under specific circumstances, if the confirmation of the diagnostic test is not received at the time the patient provides a prescription for the therapeutic agent to the dispenser/pharmacy. In some embodiments, a method includes receiving, at a host device of the RMS, for a therapeutic agent associated with at least one indication, a request from a compute device associated with a pharmacy enrolled in the RMS to dispense a first quantity of the therapeutic agent to a patient enrolled in the RMS. The method includes generating a first authorization code if a confirmation of a successful diagnostic test of the patient was received from a prescriber enrolled in the RMS within a first predetermined time period. A second authorization code is generated if at least one of the following is true: (1) the confirmation of the successful diagnostic test of the patient is not received within the first predetermined time period, and the request from the compute device associated with the pharmacy is received within a second predetermined time period; or (2) a request is received from a compute device associated with the prescriber to dispense a second quantity of the therapeutic agent to the patient and different from the first quantity. The method further includes generating a third authorization code if the confirmation of the successful diagnostic test of the patient was not received within the first predetermined time period and if the request from the compute device associated with the prescriber to dispense the second quantity of the therapeutic agent is not received. The first authorization code, the second authorization code, or the third authorization code is provided to the compute device associated with the pharmacy.

Aspects of the systems, devices, and methods described herein are further operable for multiple indications. At least some of the multiple indications can be associated with different enrollment periods for a patient. In some embodiments, a method includes receiving, at a host device of a RMS for a therapeutic agent associated with multiple indications and from a prescriber, a request to enroll a patient in the RMS. The request can include a specification of an indication and can further include a confirmation of a diagnostic test conducted on the patient. The diagnostic test is associated with the therapeutic agent and the indication. The method also includes enrolling, at the host device, in response to the request, the patient in the RMS. The enrolling can include identifying a predetermined enrollment period based on the indication. The predetermined enrollment period can have a first duration when the indication is a first indication from the multiple indications. The predetermined enrollment period can have a second duration different from the first duration when the indication is a second indication from the multiple indications. The method also includes generating, based on the predetermined enrollment period, an authorization code indicating whether the patient is authorized to receive the therapeutic agent.

Aspects of the systems, devices, and methods described herein are further operable to ensure that a patient is enrolled in the RMS for the correct indication (from multiple indications associated with a therapeutic agent) and duration, prior to dispensing the therapeutic agent to the patient for the indication. In some embodiments, a method includes receiving, at a host device of a RMS for a therapeutic agent associated with multiple indications and from a compute device associated with a pharmacy enrolled in the RMS, a request to dispense a quantity of the therapeutic agent to a patient not enrolled in the RMS. The request can include a specification of an indication. If the request meets a patient enrollment criterion associated with the indication, a first authorization code can be generated, and the patient can be enrolled in the RMS for a first duration at the host device and in response to the request. If the indication is a second indication and the request meets a patient enrollment criterion associated with the second indication, a second authorization code can be generated, and the patient can be enrolled in the RMS for a second duration different from the first duration at the host device and in response to the request. The method can also include providing the first authorization code or the second authorization code to the compute device associated with the pharmacy.

In some embodiments, a method includes receiving, at a host device of a RMS for a therapeutic agent associated with multiple indications and from a prescriber, a request to enroll a patient in the RMS. The request can include a specification of an indication and can further include a confirmation of a diagnostic test conducted on the patient. The diagnostic test can be associated with the therapeutic agent and the indication. The method can also include enrolling, at the host device, in response to the request, the patient in the RMS. The enrolling can include identifying a predetermined enrollment period based on the indication. The predetermined enrollment period can have a first duration when the indication is a first indication. The predetermined enrollment period can have a second duration different from the first duration when the indication is a second indication. The method can also include generating, based on the predetermined enrollment period, an authorization code indicating whether the patient is authorized to receive the therapeutic agent.

Aspects of the systems, devices, and methods described herein are further operable to ensure that a patient enrolled in the RMS for one of several indications associated with a therapeutic agent can, in some embodiments, continue to receive the therapeutic agent even if the patient does not meet a dispensation criterion (e.g., confirmation of a diagnostic test) for the indication/therapeutic agent, but does meet a dispensation criterion for another of the indications. In some embodiments, a method includes receiving, at a host device of a RMS, for a therapeutic agent associated with multiple indications, a request from a compute device associated with a pharmacy enrolled in the RMS to dispense the therapeutic agent to a patient enrolled in the RMS. The request can include an identifier of a first indication. The method can also include generating, at the host device, an authorization code associated with the patient if: (1) the request does not meet a dispensation criterion associated with the first indication and (2) the request meets a dispensation criterion associated with a second indication. The method can also include providing the authorization code to the compute device associated with the pharmacy such that the pharmacy can use the authorization code to dispense the therapeutic agent to the patient.

Aspects of the systems, devices, and methods described herein are further operable to ensure that a patient is enrolled in the RMS for the correct indication as well as to ensure that the patient has requested (and receives) a correct form of the therapeutic agent (e.g., a correct quantity, dosage, frequency, strength, number of tablets, type of medication (tablets, liquid, capsule, etc.) etc.). In some embodiments, a method includes receiving, at a host device of a RMS for a therapeutic agent associated with multiple indications and from a compute device associated with a pharmacy enrolled in the RMS, a request to dispense a quantity of the therapeutic agent to a patient not enrolled in the RMS. The request can include a specification of an indication. If (1) the indication is a first indication, (2) the request meets a patient enrollment criterion associated with the first indication, and (3) the quantity meets a dispensation criterion associated with the therapeutic agent for the first indication, the host device can generate a first authorization code, and can enroll in response to the request, the patient in the RMS for a first duration. If (1) the indication is a second indication, (2) the request meets a patient enrollment criterion associated with the second indication, and (3) the quantity meets a dispensation criterion associated with the therapeutic agent for the second indication, the host device can generate a second authorization code, and can enroll, in response to the request, the patient in the RMS for a second duration different than the first duration. The method can further include providing the first authorization code or the second authorization code to the compute device associated with the pharmacy. In some embodiments, enrolling a patient in a RMS can include, for example, activating a previous enrollment, re-enrolling the patient in the RMS, extending a duration of an enrollment period for a patient in the RMS, and/or the like.

As used in this specification, the singular forms "a," "an" and "the" include plural referents unless the context clearly dictates otherwise. Thus, for example, the term "a network" is intended to mean a single network or a combination of networks.

FIG. 1 is a schematic illustration of a system within which aspects of a RMS host device 100 (hereon "host device") can be implemented and employed for one or more therapeutic agents, and for one or more indications. The host device 100 is operable for use by entities (illustrated in FIG. 1 in singular, for simplicity) such as one or more prescribers 112, one or more patients 114, and one or more dispensers 116 for risk management of one or more therapeutic agents. In some embodiments, the host device 100 is owned by, managed by, and/or otherwise associated with one or more manufacturers and/or distributors of the one or more therapeutic agents; in other words, any entity in the business-to-business distribution chain, not including the last entity that is involved in the business-to-patient dispensing of the one or more therapeutic agents.

It is understood that the prescriber 112, the patient 114, and/or the dispenser 116 can represent human entities, hardware/software interfaces (e.g., a compute device, a land or mobile phone, a web interface, and/or the like) interacting with the host device 100, and/or the like. For example, the prescriber 112 can encompass a web browser-based interface and/or a cloud-based application for administering a certification test to the prescriber (described later), an office phone of the prescriber for requesting diagnostic test confirmation (described later), and/or the like. In another example, the dispenser 116 can encompass a web browser-based interface for providing codes (described later) to the dispenser for dispensing the therapeutic agent(s) to the patient 114. In this manner, the distinction between these entities, and particularly between the prescriber 112 and the dispenser 116, can be simply functional; said another way, it is conceivable that the same entity can both prescribe and dispense the drug, but would interact with the host device 100 via different interfaces.

The host device 100 can be in communication with the prescriber 112, the patient 114, and/or the dispenser 116 as indicated by solid lines in FIG. 1 via, for example, one or more networks, each of which can be any type of network such as, for example, a local area network (LAN), a wide area network (WAN), a virtual network, a telecommunications network, and/or the Internet, implemented as a wired network and/or a wireless network. Any or all communications can be secured (e.g., encrypted) or unsecured, as is known in the art. The host device 100 can be a personal computer, a server, a work station, a tablet, a mobile device, a cloud computing environment, an application or a module running on any of these platforms, and/or the like. The dotted lines indicate communications and/or other interactions between the prescriber 112, the patient 114, and/or the dispenser 116 that do not necessarily take place via the host device 100 such as, for example, a prescriber 112 calling in a prescription to the dispenser 116 over a telephone for the patient 114.

The host device 100 includes at least a processor 110 (also sometimes referred to as a "RMS processor") and a memory 160. FIG. 1 also illustrates a database 170 (also sometimes referred to as a "RMS database"), although it will be understood that, in some embodiments, the database 170 and the memory 160 can be a common data store. In some embodiments, the database 170 constitutes one or more databases. Further, in other embodiments (not shown), at least one database can be external to the host device 100. FIG. 1 also illustrates an input/output (I/O) component 180, which can depict one or more input/output interfaces, implemented in software and/or hardware, for the prescriber 112, the patient 114, the dispenser 116, and/or other entities to interact directly or indirectly with the host device 100.

The memory 160 and/or the database 170 can independently be, for example, a random access memory (RAM), a memory buffer, a hard drive, a database, an erasable programmable read-only memory (EPROM), an electrically erasable read-only memory (EEPROM), a read-only memory (ROM), Flash memory, and/or so forth. The memory 160 and/or the database 170 can store instructions to cause the processor 110 to execute modules, processes and/or functions associated with the host device 100.

The processor 110 includes a business module 122, a prescriber module 124, a patient module 126, a dispenser module 128, an authorization module 130, a database module 136, and a communication module 140. In some embodiments, the processor 110 can include additional modules (not shown). Each module can independently be a hardware module and/or a software module (implemented in hardware, such as the processor 110).

In some embodiments, the functionality of one or more of the modules can be combined and/or overlap. For example, the communication module 140 and the database module 140 can be a single module. In some embodiments, the functionality of one or more modules and/or the interaction between the modules can be based on regulatory requirements for data processing, storage, integrity, security, and/or the like.

The processor 110 can be, for example, a general purpose processor, a Field Programmable Gate Array (FPGA), an Application Specific Integrated Circuit (ASIC), a Digital Signal Processor (DSP), and/or the like. The processor 110 can be configured to run and/or execute application processes and/or other modules, processes and/or functions associated with the device 100 and/or the network. Any of the prescriber 112, the patient 114, the dispenser 116 can also includes a memory and a processor (not shown in FIG. 1).

The communication module 140 can be operable to facilitate network connectivity for the host device 100 as is known in the art. For example, the communication module 140 can include and/or enable a network interface controller (NIC), wireless connection, a wired port, and/or the like. As such, the communication module 140 can establish and/or maintain a communication session with the prescriber 112, the patient 114 and/or the dispenser 116. Similarly stated, the communication module 140 can enable the RMS host device 110 to send data to and/or receive data from the prescriber 112, the patient 114 and/or the dispenser 116.

The database module 136 is operable for interfacing with the memory 160 and/or the database 170 for data manipulation (including storage, modification, and/or deletion). For example, the database module 136 can be operable for storing a prescriber profile of the prescriber 112 in the memory 160, for storing a patient profile of the patient 114 in the database 170, and/or the like. In another example, the database module 136 can be operable for storing a patient profile in the database 170 and/or modifying a patient profile stored in the database 170 to change the patient's status from active to inactive (described in further detail herein). In yet another example, the database module 136 can be operable to delete or update (e.g., set an inactive flag) a dispenser profile associated with the dispenser 116 and stored in the database 170 when the dispenser fails to reenroll with the host device 100 before expiration of a dispenser enrollment period.

The business module 122 is operable to facilitate control of the host device 100, including viewing and manipulating the memory 160 and/or the database 170. In some embodiments, and as will be described in more detail herein, the business module 122 can be further operable to facilitate entry of information by a user (not shown), such as a telephone operator, a third party compute device, and/or the like, associated with the host device 100, where the user in turn interacts with the prescriber 112, the patient 114, and/or the dispenser 116.

In some embodiments, the prescriber module 124 is operable to enroll the prescriber 112 with the host device 100 for one or more of the therapeutic agents. In some embodiments, the one or more therapeutic agents include N-(4-{[(5R)-7-chloro-5-hydroxy-2,3,4,5-tetrahydro-1H-1-benzazepin-1-yl]carbonyl}-3-methylphenyl)-2-methylbenzamide, or tolvaptan ("tolvaptan" hereon). In some embodiments, the one or more therapeutic agents include different formulations and/or uses of tolvaptan. In some embodiments, the different formulations and/or uses of tolvaptan are directed to different indications. In some embodiments, at least one of the indications is hyponatremia. In some embodiments, at least one of the indications is autosomal dominant polycystic kidney disease (ADPKD).

In some embodiments, the prescriber module 124 is operable to directly receive a request from the prescriber 112 to be enrolled via any suitable means, such as, for example, via a web interface of the prescriber module 124. In other embodiments, the prescriber module 124 receives a request to enroll the prescriber 112 indirectly. For example, in some embodiments, the prescriber 112 provides an enrollment request via a mail-in form, a facsimile form, or via a telephone call. In such embodiments, the enrollment request can be entered into the host device 100 via the business module 122 (e.g., by a user interacting directly with the host device), and subsequently and/or indirectly be received by the prescriber module 124.

In some embodiments, the enrollment request includes prescriber enrollment information. In some embodiments, the prescriber enrollment information is received as part of an enrollment form reviewed and completed by the prescriber 112. In some embodiments, an empty prescriber enrollment form is provided to the prescriber 112 in response to the enrollment request, and the enrollment information/completed enrollment form is received in response to the empty enrollment form being provided. In some embodiments, the enrollment request is specific for one or more therapeutic agents and/or indications, and subsequent enrollment activity is directed towards enrolling the prescriber 112 with the host device 100 for the specific therapeutic agent(s) and/or indication(s).

Explained hereon with respect to one specific therapeutic agent for simplicity, in some embodiments, in response to an enrollment request for a therapeutic agent, the prescriber module 124 is operable to provide educational information and certification information to the prescriber 112, such as via a web interface, email, and/or the like. In other embodiments, a user of the device 100 is prompted (via the business module 122) to provide printed education information and certification information to the prescriber 112, such as, for example, via postal mail, or via facsimile.

In some embodiments, the educational information includes one or more of the following: prescription information for the therapeutic agent, prescriber compliance requirements for enrollment, one or more indications associated with the therapeutic agent, one or more side effects associated with the therapeutic agent, adverse event reporting information for the therapeutic agent (whether associated with the one or more indications or otherwise), a listing of additional educational resources, diagnostic testing requirements for patients enrolled in the RMS system, and/or the like. The prescription information can include, but is not limited to, patient enrollment/discontinuation information, patient counseling information, diagnostic test ordering information, diagnostic test reviewing information, diagnostic test reporting/confirmation information, patient re-enrollment information, and/or the like. In some embodiments, the educational information is in the form of a letter, an online form, an email message, an interactive (online or in-person) question and answer session, and/or the like. In embodiments where the enrollment request specifies two or more therapeutic agents, the educational information can encompass the specified therapeutic agents.

The certification information can include access information for a certification test that is related to the educational information. In some embodiments, the access information includes a unique link and/or identifier for accessing a web-based certification test that is conducted by the prescriber module 122. In some embodiments, a third-party can administer the prescriber certification test, either directly via the host device 100 or indirectly (not shown) from a server and/or host device associated with the third-party. In other embodiments, the third-party can manually administer the test (e.g., at a testing center, at the prescriber's office, etc.).

In other embodiments, the access information includes a telephone number where the prescriber 112 can call in and take a phone-based automated or manually administered certification test. In some embodiments, the access information is a fillable request (e.g., a prepaid postcard) for a paper copy of the certification test to be mailed to the prescriber 112. In some embodiments, the certification information can include the certification test. In some embodiments, the duration of enrollment of the prescriber 112 is based on the performance of the prescriber (e.g., a higher score results in a greater duration of enrollment than a lower score, and vice versa). For example, if the prescriber's score is above a first threshold but below a second threshold, the prescriber can be authorized to prescribe the therapeutic agent for a first time period. If, however, the prescriber's score is above both the first threshold and the second threshold, the prescriber can be authorized to prescribe the therapeutic agent for a second time period greater than the first time period.

The certification test can includes questions in any suitable format (e.g., multiple choice questions, short answers, and/or the like) that test the prescriber's ability to understand the educational information. In some embodiments, the prescriber module 122 is operable to wholly analyze the performance of the prescriber 112 on the certification test (e.g., responses to multiple choice questions, via automated textual analysis, and/or the like). In other embodiments, the prescriber module 124 analyzes a portion of the certification test, and receives an analysis of a remainder portion of the certification test from another entity (e.g., an external testing entity, a user of the device 100, and/or the like). In yet another embodiment, the prescriber module 124 communicates the prescriber's responses to the certification test to another entity that analyzes the responses (not shown).

In some embodiments, analysis of the certification test yields an identifier of the performance of the prescriber 112. In some embodiments, the identifier is a sliding scale (e.g., 43% correct, 56/100 correct, and/or the like) or a discrete scale (e.g., 30-40% correct, 50-60 correct, and/or the like) measure of the performance of the prescriber 112. In some embodiments, the identifier is a binary identifier of the performance of the prescriber 112 such as, for example, whether the prescriber achieved a threshold score ("pass") or not ("fail"). In some embodiments, the threshold score can be a perfect score (i.e., 100% correct). In some embodiments, the certification test includes several sections, and the identifier can be a combination of identifiers for each section, or a single identifier across multiple sections.

In some embodiments, the prescriber module 124 is operable to enroll the prescriber 112 in the host device 100 if the performance of the prescriber meets a performance criterion for the certification test. The performance criterion for the certification test, or for a section thereof, can be one or more of the following: a threshold measure (e.g., at least 60%), a binary measure (e.g., must achieve a "pass" score, as discussed above), and/or the like.

In some embodiments, enrolling the prescriber includes providing the prescriber enrollment form to the prescriber 112 via the prescriber module 112, and/or receiving the completed enrollment form from the prescriber, either directly or indirectly via the prescriber module 112. The enrollment form can include fields for one or more of the following: the prescriber's name, a registration identifier for the prescriber such as a national provider identifier NPI), contact information, credentials, specialty, consent to a contractual agreement provided for in the enrollment form, and/or the like.

In some embodiments, the prescriber module 124 is further operable to, in response to receiving the enrollment form, generate a certification identifier for the prescriber 112. The prescriber module 124 is further operable to generate a prescriber profile for the prescriber 112, and to store the prescriber profile in the memory 160 and/or the database 170 (e.g., via the database module 136). The prescriber profile can include, but is not limited to, the prescriber enrollment information, the certification identifier, the therapeutic agent(s) and/or indication(s) for which the prescriber 112 is enrolled, a duration of enrollment of the prescriber for each therapeutic agent, a date of the last passed certification test, and/or the like.

Although described herein with respect to embodiments where the prescriber 112 requests to be enrolled, in other embodiments, the prescriber module 124 is operable to invite the prescriber to enroll by providing to the prescriber, without any input from the prescriber, the educational information and the certification information. The prescriber 112 can then take the certification test and be enrolled in a manner similar to as described above.

In some embodiments, the enrollment of the prescriber 112 with the RMS does not expire within a specific time period. In some embodiments, the enrollment of the prescriber 112 with the RMS expires at the end of a prescriber enrollment period, and the prescriber module 124 is operable to remind the prescriber to re-enroll when the prescriber's enrollment period is about expire. The prescriber 112 can then opt to re-enroll prior to expiration. In some embodiments, the prescriber 112 is required to re-take the certification test and/or take a different certification test for re-enrollment, while in other embodiments, prescriber re-enrollment does not require completing an assessment.

In some embodiments, the patient module 126 is operable to receive, via a communication network and from the prescriber 112 or a compute device associated with a prescriber 112, a request to enroll a patient in a RMS program of a therapeutic agent associated with multiple indications. The request can include a specification of at least one indication. In some embodiments, the request can also include a confirmation of a diagnostic test conducted on the patient, where the diagnostic test is associated with the therapeutic agent and with the indication. In some embodiments, the patient module 126 is operable to enroll the patient 114 with the host device 100 for one or more of the therapeutic agents and/or for one or more indications. In some embodiments, the patient module 126 is operable to provide a patient enrollment form to the patient 114 and/or the prescriber 112, and to receive patient enrollment information from the patient 114 and/or the prescriber 112.

In some embodiments, the patient module 126 is operable to provide the patient enrollment form to the prescriber 112. Said another way, in such embodiments, the prescriber 112 enrolls the patient 114, after counseling the patient and obtaining the patient's consent to treatment by the prescriber. In such embodiments, the patient module 126 is operable to provide patient education information and the patient enrollment form to the prescriber 112, either directly or via the prescriber module 124. The prescriber 112 in turn, and in accordance with the prescriber enrollment form described above, can communicate the patient education information to the patient via any suitable means, including verbally, electronically, via printouts, and/or the like. Although described herein for patient enrollment, the patient enrollment form can also be employed for patient reenrollment (e.g., each time the patient enrollment expires).

In some embodiments, the patient enrollment form can require a certification, by the prescriber 112, of a diagnostic test conducted on the patient 114 to monitor the potential for and/or the actual occurrence of adverse side effects related/unrelated to the therapeutic agent(s). In such embodiments, the prescriber 112 can obtain the diagnostic test results in any suitable manner such as, but not limited to, conducting the diagnostic test himself, ordering the diagnostic test to be conducted at a testing facility and subsequently reviewing the results, and/or the like. In some embodiments (not detailed here), the prescriber 112 can order the diagnostic test via the host device 100, such as, for example, via an ordering module (not shown). In some embodiments, the patient 114 can choose where to be tested, and can arrange for the prescriber 112 to receive the diagnostic test results. In some embodiments, the diagnostic test is a liver function test (LFT). In some embodiments, the LFT measures plasma levels of one or more of total bilirubin, alanine aminotransferase, and aspartate aminotransferase.

The patient enrollment form can include patient identification information, patient contact information, an indication of whether the patient is being enrolled for the first time or reenrolled, one or more indications for which the patient is being treated, a consent of the patient to treatment and treatment-related issues such as diagnostic testing, one or more diagnostic test results of the patient, a certification from the prescriber that the diagnostic test results are satisfactory, and/or the like. The patient module 126 is further operable to receive the completed patient enrollment form, directly, or via the prescriber module 124, or via the business module 122 (e.g., when the prescriber 112 sends in a completed form via postal mail, or via facsimile, that is subsequently entered into the device 100).

In other embodiments, the patient module 126 is operable to determine, based on the patient enrollment form or otherwise, whether the patient is a new patient (i.e., no existing patient profile), a currently enrolled patient (i.e., associated with an active patient profile), or a previously enrolled patient (i.e., associated with an inactive patient profile). In some instances, the patient 114 is a new patient, the patient module 126 is operable to generate a new patient profile for the patient based on the completed enrollment form, and is operable to store the patient profile in the memory 160 and/or the database 170 (e.g., via the database module 136). In some embodiments, the patient module 126 generates the patient profile by identifying a predetermined enrollment period/duration of enrollment based on the indication. The predetermined enrollment period can have different durations for different indications. For example, in some embodiments, the predetermined enrollment period has a first duration for a first indication, a second duration different from the first duration for a second indication, and so on.

The patient profile can include, but is not limited to, the patient enrollment information, the therapeutic agent(s) for which the patient 114 is enrolled, prescribing information for the patient, a duration of enrollment of the patient, one or more prescribers associated with the patient profile, a current status of the patient profile (active/inactive), one or more indication(s) associated with the patient, and/or the like. In some embodiments, the prescribing information, such as dosage, quantity, duration, number of refills, etc. is predetermined and cannot be specified by the prescriber 112.

In some instances, the patient is a currently enrolled patient having an existing (active) patient profile, and the patient module 126 is operable to update the existing patient profile with the information the received patient enrollment form. Such instances can occur, for example, when the patient is reenrolled prior to expiration of a previous enrollment period, when the patient switches to a different prescriber for the same therapeutic, and so on.

In some instances, the patient was previously enrolled but treatment was discontinued, the patient accordingly has an inactive patient profile associated therewith, the patient module 126 is operable to update the existing patient profile with the information from the received patient enrollment form, and to change the status of the updated patient profile to active. Such instances can occur when, for example, the patient re-continues treatment, switches from one therapeutic agent to another therapeutic agent that is also managed by the host device 100, receives treatment for a different indication, and so on.

In some embodiments, the patient module 126 is further operable to receive periodic confirmation of satisfactory diagnostic test results for the patient 114 from the prescriber 112 for continued dispensing of the therapeutic agent. In some embodiments, a confirmation of a satisfactory diagnostic test result is required each time the therapeutic agent is dispensed to the patient 114. In other embodiments, a confirmation of a satisfactory diagnostic test result is not required each time the therapeutic agent is dispensed to the patient 114. For example, a confirmation of a satisfactory diagnostic test result can be required the first time the therapeutic agent is dispensed, and then be required for every two refills, and then be required again if/when the patient is reenrolled. In some embodiments, the frequency at which satisfactory diagnostic results need be provided can be based on the indication associated with the therapeutic agent. In some embodiments, the patient module 126 is operable to store the confirmation(s) of diagnostic test results in the memory 160 and/or the database 170 as part of the patient profile, or associated with the patient profile. In other embodiments, the patient module 126 is operable to store the values of the diagnostic test results in the memory 160 and/or the database 170 as part of the patient profile, or as associated with the patient profile.

In some embodiments, the confirmation of satisfactory diagnostic test results is received as a test confirmation form that is completed by the prescriber 112. The test confirmation form can include fields for patient information, prescriber information, testing information, and/or the like. The testing information can include test dates, a certification of the test results by the prescriber 112, a certification by the prescriber of whether the patient should continue to receive the therapeutic agent or not, and/or the like. In some embodiments, the testing information can also include values of test results such as, for example, blood levels of an analyte and/or the like. The test confirmation form can be received electronically from the prescriber 112 by the host device 100, or entered indirectly (e.g., manual entry of a test confirmation form received via postal mail, or via facsimile).

Hence, it is understood that the prescriber 112 can provide the confirmation of the diagnostic test results to the host device 100 either via the patient enrollment form, or via a separate test confirmation form, or both. When the duration of patient enrollment is substantially similar to the periodicity of diagnostic testing and/or dispensing, the prescriber 112 can report test results during reenrollment via a single form. When the duration of patient enrollment is substantially longer (e.g., a year) compared to the periodicity of diagnostic testing and/or dispensing (e.g., every 30 days), the prescriber 112 can personally meet with the patient 114 once a year to complete the patient enrollment/re-enrollment form (which can include the signature/consent of the patient), and thereafter can submit the test confirmation form upon reviewing the patient's diagnostic test results, which need not include the patient's presence/consent.

In some embodiments, the duration of patient enrollment, the periodicity of the diagnostic test, the periodicity of dispensing the therapeutic agent, and/or the duration for which a prescription is provided (including refills), can each be different. As an example, the prescriber 112 can provide the confirmation of the diagnostic test results via the patient enrollment form at the time of enrollment of the patient 114 in the RMS for one year (or other suitable time frame). In such an example, the patient can receive a refill for the therapeutic agent every month after undergoing monthly diagnostic tests. In some embodiments, the duration for which a prescription is provided is three months (e.g., one month supply with two refills). In this example, the prescriber 112 can write a prescription for a one-month supply with two refills and can provide confirmation of diagnostic test results when enrolling or reenrolling (e.g., after one year or other suitable timeframe) the patient 114. The patient 114 can receive the initial one-month supply after being enrolled in the RMS. The patient 114 can receive each of the two refills without visiting the prescriber 112 by receiving a diagnostic test and having the prescriber 112 confirm the diagnostic test result. In such an example, the patient 114 can visit the prescriber 112 every three months to receive a new prescription for three months (one-month supply with two refills). Since the duration of patient enrollment is one year in this example, the patient 114 can meet with the prescriber 112 initially to be enrolled and/or reenrolled as well as three additional times during the enrollment period.

For another example, the prescriber 112 can provide the confirmation of diagnostic test results via the patient enrollment form at the time of enrollment of the patient 114 for a year. In such an example, the patient receives a refill for the therapeutic agent every month (i.e., 11 refills), and diagnostic tests are conducted every three months. In this example, the prescriber 112 can order and review diagnostic test results every three months without necessarily interacting with the patient, and the patient 114 can receive every third refill after providing satisfactory diagnostic test results. For other refills, no action is taken by the prescriber. If the prescriber decides to re-enroll the patient for another year, the prescriber can again meet with the patient, order and review a diagnostic test, and complete the patient re-enrollment form.

In some embodiments, the patient module 126 is further operable to issue periodic reminders to the prescriber 112 associated with the patient 114 if the test confirmation form is not received within a specified time period since a previous event. The previous event can be the last time the patient 114 received the therapeutic agent, the last time a test confirmation form was received for the patient from the prescriber 112, and/or the like. The reminders can be issued automatically (e.g., by the host device 100), or manually (e.g., by the dispenser 116). In some embodiments, the reminders are communicated via any suitable means specified by the prescriber 112 at the time of creating the prescriber profile, such as via email, text message, an automated telephone call, an automated facsimile, a notification via a cloud-based application on the prescriber's smart phone, and/or the like. In some embodiments, the periodicity of the reminders and/or the determination of whether to issue a reminder or not can be based on an elapsed duration of enrollment of the patient, a remaining duration of enrollment of the patient, a remaining time for the specified time period, the therapeutic agent, one or more indications associated with the therapeutic agent, and/or the like. For example, if the prescriber is supposed to turn in a test confirmation form once a month, a reminder can be issued once a week for the first two weeks since the last time a test confirmation form was turned in, twice in the third week, and every other day in the fourth week. In another example using a similar scenario, the prescriber receives email reminders in the first two weeks, text message reminders in the third week, and automated telephone calls in the fourth week.

In some embodiments, the patient module 126 is further operable to receive, without receiving the test confirmation form, a dispensing request for the therapeutic agent from the prescriber 112 for the patient 114. In some embodiments, the dispensing request is indicative of an authorization from the prescriber 112 for the dispenser 116 to dispense a limited quantity of the therapeutic agent to the patient 114. In this manner, the prescriber 112 can authorize the dispenser 116 to provide the therapeutic agent to the patient 114 under a number of circumstances such as, for example, when the patient communicates a delay in providing diagnostic test results to the provider, when the provider has not had an opportunity to substantially review received diagnostic test results, and/or the like. In some embodiments, the prescriber 112 can provide the dispensing request in response to a reminder from the patient module 126 to submit the test confirmation form. In some embodiments, the prescriber 112 is permitted to issue a limited number of dispensing requests per patient enrollment period. In some embodiments, the prescriber is not permitted to issue consecutive dispensing requests without submitting a test confirmation form in between.

The prescriber 112 can provide the dispensing request in any suitable form, such as via a web interface, via a reply to an email or a text message, via a telephone call, via facsimile, and/or the like. In some embodiments, the patient module 126 can associate a dispensing request for the patient 114 with the patient profile for the patient.

In some embodiments, the patient module 126 is further operable to receive one or more adverse event reports for the patient 114 from the prescriber 112, from the patient 114, and/or from the dispenser 116. In some embodiments, the patient module 126 is operable to store the adverse event report in the memory 160 and/or the database 170 as part of the patient profile, or as associated therewith. In some embodiments, the patient module 126 is operable to change the status of the patient profile from active to inactive based on the adverse event report.

In some embodiments, the adverse event report is received as a completed adverse event reporting form. The adverse event reporting form can include fields for patient information, information about the reporting entity, and/or the like. The adverse event reporting form and/or information can be received electronically directly from the prescriber 112 by the host device 100, or entered indirectly (e.g., manual entry). The adverse event report(s) can be stored in the memory 160 and/or the database 170. In some embodiments, specific types of adverse events, such as unsatisfactory diagnostic test results, are written in adverse event reporting form and stored in the memory 160 and/or the database 170. In some embodiments, other types of adverse events can be reported directly to manufacturer(s) of the therapeutic agent(s).

In some embodiments, the stored adverse event reports are searchable by the prescriber 112, the patient 114, the dispenser 116 and/or other entities (not shown) such as researchers, regulatory bodies, other prescribers/patients/dispensers not associated with the host device 100, and/or the like. In some embodiments, the host device 100 can be operable to combine, compile, interlink, and/or otherwise manipulate the stored adverse event reports. In some embodiments, the results of such operations can be searchable as described above. In some embodiments, these operations can be performed by an adverse event reporting module (not shown) of the processor 110.

In some embodiments, the patient module 126 is further operable to remind the prescriber 112 and/or the patient 114 to re-enroll the patient when the patient's enrollment period is about expire. The prescriber 112 can then communicate with the patient 114, complete a new patient enrollment form, and re-enroll the patient prior to expiration. As noted earlier for reminders for confirmation forms, reminders can be issued automatically (e.g., by the host device 100), or manually (e.g., by a telephone operator associated with the host device 100). In some embodiments, the reminders are communicated via any suitable means specified by the prescriber 112 at the time of creating the prescriber profile, such as via email, text message, an automated phone call, an automated facsimile, a notification via a cloud-based application on the prescriber's smart phone, and/or the like. In some embodiments, the periodicity of the reminders and/or the determination of whether to issue a reminder or not can be based on one or more of the following: an elapsed duration of enrollment of the patient, a remaining duration of enrollment of the patient, the specific quantity of the therapeutic agent received by the patient till date (e.g., after the patient receives his last refill), the therapeutic agent, one or more indications associated with the therapeutic agent, and/or the like.

In some embodiments, the dispenser module 128 is operable to enroll the dispenser 116 with the host device 100 for one or more of the therapeutic agents. In some embodiments, the dispenser 116 operates in an out-patient setting and/or dispenses directly to patients, such as a retail pharmacy. In some embodiments, the dispenser 116 operates in an in-patient setting, such as a hospital, a care facility, a mental health facility, a prison, and/or the like.

In some embodiments, the dispenser module 128 is operable to directly receive a request from the dispenser 116 to be enrolled via any suitable means, such as, for example, via a web interface of the dispenser module 128, or via a phone call. In other embodiments, the dispenser module 126 receives a request to enroll the dispenser 116 indirectly. For example, in some embodiments, the dispenser 116 provides an enrollment request via a mail-in form, a facsimile form, or via a telephone call. In such embodiments, the enrollment request can be entered into the host device 100 via the business module 122 (e.g., by a user interacting directly with the host device), and subsequently (i.e., indirectly) be received by the dispenser module 128. In this manner, a dispenser can choose to enroll on-demand such as, for example, when the patient 114 presents a prescription for the therapeutic agent(s) to the dispenser 116.

In some embodiments, the enrollment request includes dispenser enrollment information. In some embodiments, the dispenser enrollment information is received as part of an enrollment form reviewed and completed by the dispenser 116. In some embodiments, an incomplete dispenser enrollment form is provided to the dispenser 116 in response to the enrollment request, and the dispenser enrollment information/completed dispenser enrollment form is received in response to the dispenser (e.g., pharmacist) completing the provided dispenser enrollment form. In some embodiments, the enrollment request is specific for one or more therapeutic agents and/or one or more indications, and all subsequent enrollment activity is directed towards enrolling the dispenser 116 with the host device 100 for the specific therapeutic agent(s) and/or indication(s).

Explained hereon with respect to one specific therapeutic agent for simplicity, in some embodiments, in response to an enrollment request for a therapeutic agent, the dispenser module is operable to provide educational information and certification information to the dispenser 116, such as via a web interface, email, and/or the like. In other embodiments, a user of the device 100 is prompted (via the business module 122) to provide printed education information and certification information to the dispenser 116, such as, for example, via postal mail or via facsimile.

In some embodiments, the educational information includes prescription information for the therapeutic agent, dispenser compliance requirements for enrollment, one or more indications associated with the therapeutic agent, one or more side effects associated with the therapeutic agent, adverse event reporting information for the therapeutic agent (whether associated with the one or more indications or otherwise), a listing of additional educational resources, and/or the like. In some embodiments, the educational information is in the form of a letter. In some embodiments, if the enrollment request specifies two or more therapeutic agents, the educational information can encompass the specified therapeutic agents.

The certification information can include access information for a dispenser certification test related to the educational information. In some embodiments, the access information includes a unique link and/or identifier for accessing a web-based dispenser certification test that is conducted by the dispenser module 128. In other embodiments, the access information includes a telephone number where a representative of the dispenser 114, such as a pharmacist employed by the dispenser, can call and complete a phone-based automated test. In some embodiments, a third party can administer the dispenser certification test, either directly via the host device 100 or indirectly (not shown) from a server and/or host device associated with the third-party. In other embodiments, the third-party can manually administer the test (e.g., at a testing center, at the prescriber's office, etc.). In some embodiments, the access information is a fillable request (e.g., a prepaid postcard) for a paper copy of the certification test to be mailed to the dispenser 114. In some embodiments, the certification information can include the dispenser certification test.

The dispenser certification test can includes questions in any suitable format (e.g., multiple choice questions, short answers, and/or the like) that test the representative's ability to understand the educational information. In some embodiments, the dispenser module 128 is operable to wholly analyze the performance of the dispenser's representative on the dispenser certification test (e.g., responses to multiple choice questions, via automated textual analysis, and/or the like). In other embodiments, the dispenser module 128 analyzes a portion of the certification test, and receives an analysis of a remainder portion of the certification test from another entity (e.g., an external testing entity, a user of the device 100, and/or the like). In yet another embodiment, the dispenser module 128 communicates with another entity that wholly analyzes the certification test.

In some embodiments, analysis of the certification test yields an identifier of the performance of the dispenser's representative. In some embodiments, the identifier is a sliding scale (e.g., 43% correct, 56/100 correct, and/or the like) or a discrete scale (e.g., 30-40% correct, 50-60 correct, and/or the like) measure of the performance of the dispenser's representative. In some embodiments, the identifier is a binary identifier of the performance of the dispenser's representative such as, for example, whether the dispenser's representative achieved a threshold score ("pass") or not ("fail"). In some embodiments, the certification test includes several sections, and the identifier can be a combination of identifiers for each section, or a single identifier across all sections.

In some embodiments, the dispenser module 128 is operable to enroll the dispenser 114 in the host device 100 if the performance of the dispenser's representative meets a performance criterion for the certification test. The performance criterion for the certification test, or for a section thereof, can be one or more of the following: a threshold measure (e.g., at least 60%), a binary measure (e.g., must achieve a "pass" score, as discussed above), and/or the like. In some embodiments, the duration of enrollment of the dispenser 114 is based on the performance of the dispenser's representative (e.g., a higher score results in a greater duration of enrollment than a lower score, and vice versa). For example, if the dispenser's score is above a first threshold but below a second threshold, the dispenser can be authorized to dispense the therapeutic agent for a first time period. If, however, the dispenser's score is above both the first threshold and the second threshold, the dispenser can be authorized to dispense the therapeutic agent for a second time period greater than the first time period.

In some embodiments, enrolling the dispenser 116 includes providing the dispenser enrollment form to the dispenser 116 via the dispenser module 128 and/or directly or indirectly receiving the completed enrollment form from the dispenser. The dispenser enrollment form can include an indication whether the dispenser is in an in-patient and/or outpatient setting, the dispenser facility name, the dispenser facility type (e.g., for in-patient pharmacies), a registration identifier for the dispenser, contact information, credentials, specialty, contact information for a designated representative of the dispenser, consent to a contractual agreement provided for in the dispenser enrollment form, and/or the like. In some embodiments, the contact information is included; in this manner, enrolling the dispensing facility to receive and dispense the therapeutic agent(s) effectively includes enrolling at least one pharmacist associated with the dispensing facility.

The dispenser module 128 is further operable to, in response to receiving the dispenser enrollment form, generate a certification identifier for the dispenser 112. The dispenser module 128 is further operable to generate a dispenser profile for the dispenser 116, and to store the prescriber profile in the memory 160 and/or the database 170 (e.g., via the database module 136). The dispenser profile can include, but is not limited to, the dispenser enrollment information, the certification identifier, the therapeutic agent(s) for which the dispenser 116 is enrolled, a duration of enrollment of the dispenser 116 for each therapeutic agent, the indication(s) for which the dispenser 116 is enrolled, and/or the like.

Although described herein with respect to embodiments where the dispenser 116 requests to be enrolled, in other embodiments, the dispenser module 128 is operable to invite the dispenser to enroll by providing to the dispenser and/or a pharmacist associated therewith, without input from the dispenser and/or the pharmacist, the educational information. The prescriber 112 can then opt to be enrolled in a manner similar to as described above.

The authorization module 130 can be configured to receive an authorization request from the dispenser, and generate codes to allow the dispenser to provide the therapeutic agent to the patient after verifying certain dispensing requirements, as described in further detail herein. In some embodiments the authorization module 130 can be configured to automatically generate codes to allow the dispenser to provide the therapeutic agent to the patient after verifying the certain dispensing requirements. In some embodiments, the authorization request is received from the prescriber and/or from the patient. Further operation of the authorization module 130 can, for example, be described with respect to the following non-limiting scenario. A patient 114 visits a prescriber 112, where the prescriber 112 deems that the patient 114 should be prescribed a therapeutic agent managed by the host device 100. The prescriber 112 enrolls or is already enrolled with the host device 100 for the therapeutic agent as described above, and proceeds to properly advise the patient 114, conduct required diagnostic test(s), complete and submit the patient enrollment form to the host device 100, and issue a prescription for the therapeutic agent to the patient 114. The prescriber 112 and/or the patient 114 then presents the prescription to the dispenser 116, where the dispenser enrolls or is already enrolled with the host device 100. In some embodiments, the prescription includes prescriber information (including a certification identifier of the prescriber), dispensing information, refill information and/or the like. The dispenser 116 requests authorization, from the host device 100, to dispense the therapeutic agent to the patient. In some embodiments, the dispenser 116 requests authorization over a web interface of the dispenser module 128 and/or the authorization module 130.

The authorization module 130 is then operable to receive the authorization request from the dispenser. In some embodiments, the authorization module 130 is further operable to determine if the patient 114 can receive the therapeutic agent based on whether the prescriber 112 is currently enrolled and/or authorized to prescribe the therapeutic agent. For example, in such embodiments, the authorization module 130 can access the prescriber profile of the prescriber 112 in the database 170 via the database module 136. If no such prescriber profile exists, or if the prescriber profile does not include the prescribed therapeutic agent, or if a predetermined period of time has elapsed since the prescriber's last certification test date, and so on, the authorization module 130 determine that the prescriber 112 is not authorized. In some embodiments, the prescriber profile can include a flag indicating the status of the prescriber 112 as authorized/unauthorized, as active/inactive, and/or the like, and the authorization module 130 can determine whether the prescriber is authorized based on the flag.

In some embodiments, the authorization module 130 is further operable to determine if the patient 114 can receive the therapeutic agent based on whether the dispenser 116 is currently enrolled and/or authorized to dispense the therapeutic agent, such as by, for example, accessing a dispenser profile of the dispenser in the database 170 via the database module 136.

In some embodiments, the authorization module 130 is further operable to determine if the patient 114 is authorized to receive the therapeutic agent. In some embodiments, determining whether the patient is authorized includes determining whether the patient 114 is actively enrolled with the host device 100. In some embodiments, determining whether the patient is authorized includes determining whether the prescriber 112 has provided a confirmation of a satisfactory diagnostic test result for the patient 114 as part of the patient enrollment form. In some instances, such as when the patient requests a refill of the prescription from the dispenser 116, determining whether the patient is authorized includes determining whether the prescriber 112 has provided a subsequent confirmation of a satisfactory diagnostic test result for the patient 114. In some embodiments, determining whether the patient is authorized includes determining whether the satisfactory diagnostic test result was received within a first predetermined time period such as, for example, within the past 30 days, or within 30 days from the last date of dispensing the therapeutic agent to the patient 114. In this manner, if a patient tests satisfactorily in a timely manner, he can receive the prescribed quantity.

In some embodiments, if the satisfactory diagnostic test result is not received within the first predetermined time period, determining whether the patient is authorized includes determining whether the authorization request was received within a second predetermined time period such as, for example, within 7 days from the end of the first predetermined period. In this manner, if the patient 114 has been unable to undergo diagnostic testing, and/or the prescriber 112 has been unable to provide confirmation of satisfactory diagnostic test results in a timely manner, the patient 114 can still receive a limited quantity of the therapeutic agent to avoid discontinuation of treatment.

In some embodiments, if the satisfactory diagnostic test result is not received within the first predetermined time period, the determining whether the patient is authorized includes determining whether a dispensing request is received from the prescriber 112 and associated with the patient profile of the patient 114. In this manner, a prescriber 112 can specify that the patient can receive a limited quantity of the therapeutic agent to avoid discontinuation of treatment, pending diagnostic test results. In some embodiments, the dispensing request authorizes the patient 114 to receive the therapeutic agent irrespective of how much time has elapsed since the last time the patient received the therapeutic agent. In other embodiments, the dispensing request authorizes the patient 114 to receive the therapeutic agent if the dispensing request is received in a specific timeframe such as, for example, after expiration of the first predetermined time period and/or before expiration of the second predetermined time period.

In some embodiments, the authorization module 130 is operable to generate and/or update one or more codes (in some embodiments, also referred to as 'authorization codes'). In some embodiments, the one or more codes are generated upon creation of the patient profile, and can be associated with the patient profile. For example, if the patient is to be enrolled for a year, and will receive an initial standard quantity of the therapeutic agent at enrollment, plus eleven refills, in some embodiments, twelve codes can be associated with the patient profile at the time of generation of the patient profile. Each code can be set to a prohibition and/or warning code (described in further detail herein) by default. In other embodiments, when a satisfactory diagnostic test result is received at the time of generation of the patient profile, twelve codes can be associated with the patient profile at the time of generation of the patient profile, with the first code being a standard authorization code (described in further detail herein), and the remaining codes being prohibition/warning codes. Each of the codes can then be modified based on one or more subsequent events such as, but not limited to, receipt of a diagnostic test result, receipt of an adverse event report, receipt of a dispensing request, transmission of the code to a dispenser, and/or the like. In other embodiments, the codes can be successively generated and associated with the patient profile, and updated based on the one or more subsequent events.

Describing the generation and updating of the codes in more detail, in some embodiments, the one or more codes are generated and/or updated in response to receipt of satisfactory diagnostic test results, or in response to confirmation of satisfactory diagnostic test results by a prescriber. In some embodiments, the one or more codes are generated and/or updated in response to receipt of an adverse event report. In some embodiments, the one or more codes are generated and/or updated in response to receipt of a dispensing request from the prescriber. In some embodiments, the one or more codes are generated and/or updated in response to the authorization request from the dispenser. In some embodiments, the one or more codes are updated upon transmission of the one or more codes to a dispenser. In some embodiments, the one or more codes are updated in response to confirmation of dispensing the therapeutic agent to the patient.

In embodiments where the satisfactory diagnostic test results were received within a first predetermined time period, the authorization module 130 can be operable to transmit a standard authorization code to the dispenser 116. In some embodiments, the standard authorization code (e.g., a first authorization code) is communicative of a permission for the dispenser 116 to dispense a first quantity of the therapeutic agent to the patient 114. In some embodiments, the first quantity is a prescribed and/or standard quantity.

In instances where the satisfactory diagnostic test result is not received within the first predetermined time period the authorization request was received within a second predetermined time period, the authorization module 130 can be operable to generate and transmit a temporary authorization code to the dispenser 116. In some embodiments, the temporary authorization code (e.g., a second authorization code) is communicative of a permission for the dispenser 116 to dispense a second quantity of the therapeutic agent to the patient 114. In some embodiments, the second quantity is different from the first quantity. In some embodiments, the second quantity is less than the first quantity.

In instances where the confirmation of satisfactory diagnostic test results is not received within the first predetermined time period and the dispensing request from the prescriber 112 has not been received, the authorization module 130 can be operable to generate and transmit a prohibition code to the dispenser 116. In some embodiments, the prohibition code (in some embodiments and/or instances, also referred to as a 'third authorization code') is communicative of forbidding and/or prohibiting the dispenser 116 from dispensing the therapeutic agent to the patient 114.

In some embodiments, the standard authorization, temporary authorization, and prohibition codes are different from each other. The codes can be of any suitable type as known in the art, and include alphanumeric characters, symbolic characters, images/graphic elements, and/or the like. In some embodiments, the codes are generated based on and/or able to identify prescriber enrollment information, patient enrollment information, dispenser enrollment information, the therapeutic agent, time and/or date information (associated with the diagnostic test, with the authorization request, with generation and/or transmission of the code(s), and/or the like), a random number, and/or the like.

In some embodiments, the authorization module 130 is operable to associate the generated/transmitted code with the patient profile, and/or update the patient profile with the generated/transmitted code. In some embodiments, the authorization module 130 receives confirmation of the therapeutic agent being dispensed to the patient 114, and is operable to associate the dispensing event with the patient profile (e.g., via the patient module 126). The confirmation can include dispensing information, including a time/date of dispensing, a lot number of the therapeutic agent being dispensed, and/or the like. In some embodiments, the authorization module 130 is operable to associate the dispensing event with the corresponding code authorizing the dispensing event. For example, in some embodiments, the authorization module 130 associates a lot number of the dispensed therapeutic agent with a standard authorization code, or updates the standard authorization code with the lot number (e.g., by appending the lot number to the end of the standard authorization code). In another example, the authorization module 130 associates a lot number of the dispensed therapeutic agent with a temporary authorization code, or updates the temporary authorization code with the lot number. In some embodiments, the lot number is indicative of the second quantity of the drug. For example, in some embodiments, aspects of this disclosure are operable in the scenario where the dispenser is provided the therapeutic agent for dispensing in two quantities: a first quantity and a second quantity. In this manner, dispensing the first quantity or the second quantity of the therapeutic agent to the patient can be tracked via the code associated with the dispensing event, via the lot number associated with the dispensing event, or both.

Returning to describe the business module 122, as noted about and in the descriptions of the various modules, the business module 122 can facilitate entry of information at the host device 100 by a user and/or a compute device that interacts with the prescriber 112, the patient 114, and/or the dispenser 116. For example, the user can receive prescriber enrollment forms via postal mail and then enroll the prescriber 112 by entering the information from the prescriber enrollment forms into host device 100, or at a compute device of the user and associated with the host device. For another example, the user can be a call center employee that communicates with the prescriber over the telephone, and enters the prescriber enrollment information into the host device 100 to define the prescriber profile. In this manner, aspects of this disclosure encompass any combination of different modes of interaction (electronic, verbal, telecommunication, postal, etc.) between the host device 100, the prescriber 112, the patient 114, and/or the dispenser 116.

In some embodiments, the business module 122 is further operable to periodically report adverse event reports stored in the memory 160 and/or the database 170 to a third party, such as a regulatory body. In some embodiments, the business module 122 is further operable to periodically synchronize adverse event reports for the one or more therapeutic agents and/or indications managed by the host device 100 with external adverse event databases.

Figure 2:
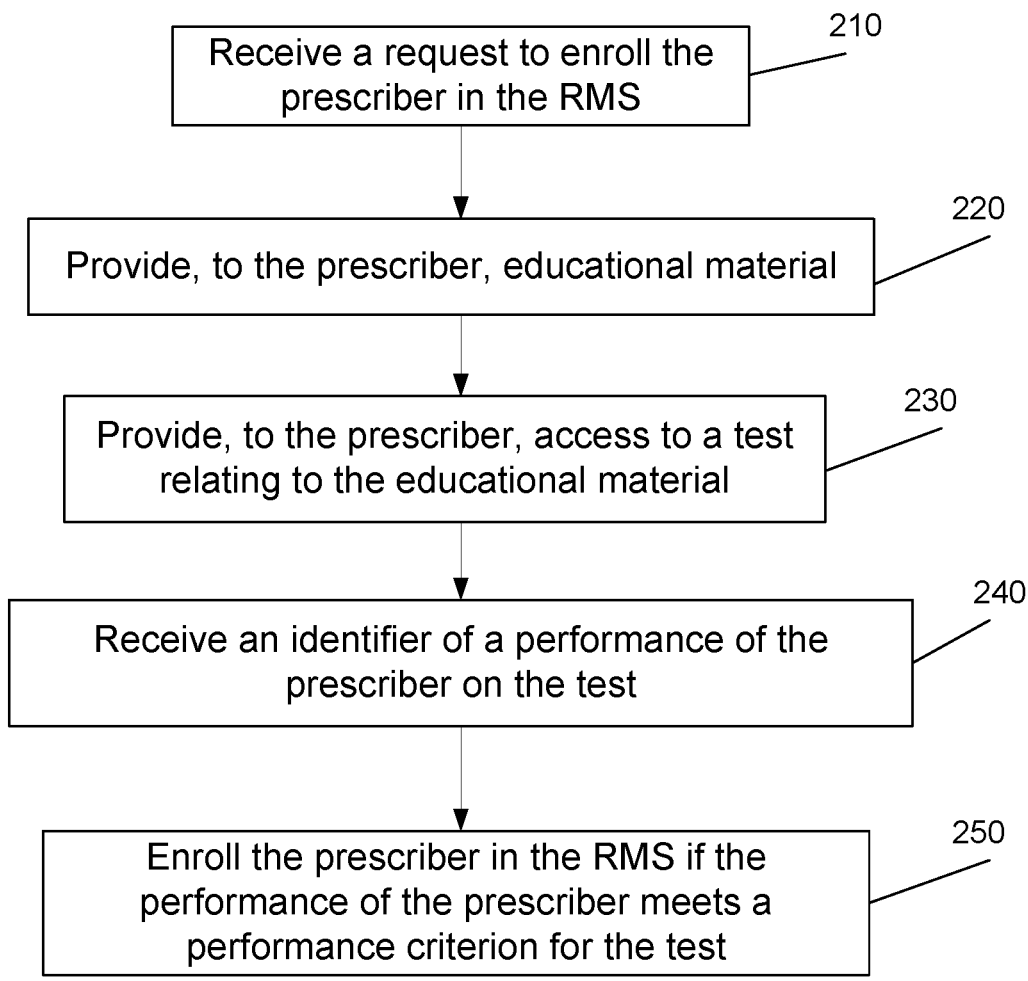
FIG. 2 is a flow chart illustrating a method of the RMS host device of FIG. 1, according to an embodiment.

Explained with reference to FIG. 1, FIG. 2 illustrates a method 200 of enrolling a prescriber, such as the prescriber 112, at the host device 100 for a therapeutic agent associated with at least one indication, according to an embodiment. In some embodiments, the therapeutic agent is tolvaptan. In some embodiments, the at least one indication includes hyponatremia. In some embodiments, the at least one indication includes autosomal dominant polycystic kidney disease (ADPKD). In some embodiments, the therapeutic agent is associated with multiple indications.

At 210, a request is received to enroll the prescriber 112 with the RMS host device 100. In response, at 220, educational information/material is provided to the prescriber 112. Further, at 230, certification information is provided to the prescriber 112 that includes, access to a certification test that is related to the educational material. The prescriber 112 takes the certification test, such as at a compute device of the prescriber, and at 240, the host device 100 receives an identifier of a performance of the prescriber on the test. At 250, the prescriber is enrolled, at the host device, in the RMS if the performance of the prescriber meets a performance criterion for the test. In some embodiments, enrolling the prescriber 112 includes authorizing the prescriber to prescribe the therapeutic agent.

In some embodiments, enrolling includes enrolling the prescriber 112 for a predetermined time period, such as a prescriber enrollment period. In some embodiments, the method 200 further includes providing, after the enrolling and to the prescriber, prior to lapse of the predetermined time period, reenrollment information associated with the RMS and with the therapeutic agent. In some embodiments, the method 200 also includes receiving consent from the prescriber in response to the reenrollment information, and reenrolling, at the host device 100, the prescriber in the RMS in response to receiving the consent.

Figure 3:
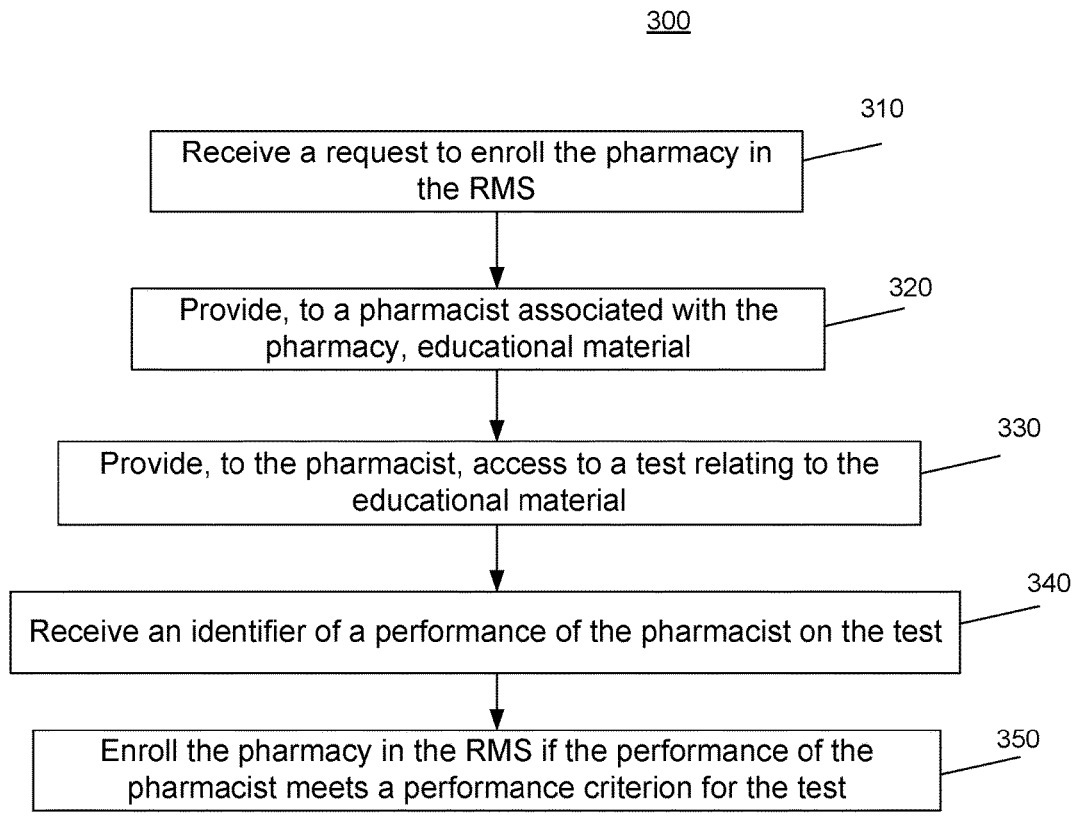
FIG. 3 is a flow chart illustrating a method of the RMS host device of FIG. 1, according to another embodiment.

Explained with reference to FIG. 1, FIG. 3 illustrates a method 300 of enrolling a pharmacy, such as the dispenser 116, at the host device 100 for a therapeutic agent associated with at least one indication, according to an embodiment. In some embodiments, the therapeutic agent is tolvaptan. In some embodiments, the at least one indication includes hyponatremia. In some embodiments, the at least one indication includes autosomal dominant polycystic kidney disease (ADPKD). In some embodiments, the therapeutic agent is associated with multiple indications.

At 310, a request is received at the RMS host device 100 to enroll the pharmacy in the RMS. At 320, educational information/material is provided to a pharmacist associated with the pharmacy. Further, at 330, the pharmacist/pharmacy is provided access to a certification test related to the educational material. The pharmacist takes the test, and at 340, an identifier of a performance of the pharmacist on the test is received by the host device 100. At 350, the pharmacy is enrolled in the RMS if the performance of the pharmacist meets a performance criterion for the certification test. In some embodiments, enrolling the pharmacy includes authorizing the pharmacy to dispense the therapeutic agent.

In some embodiments, enrolling the pharmacy includes enrolling the pharmacy for a predetermined time period, such as a dispenser enrollment period. In some embodiments, the method 300 further includes providing, after the enrolling, and to the pharmacist prior to lapse of the predetermined time period, reenrollment information associated with the RMS and with the therapeutic agent. The method also includes receiving consent from the pharmacist in response to the reenrollment information and reenrolling the pharmacist in the RMS in response to receiving the consent.

Figure 4:
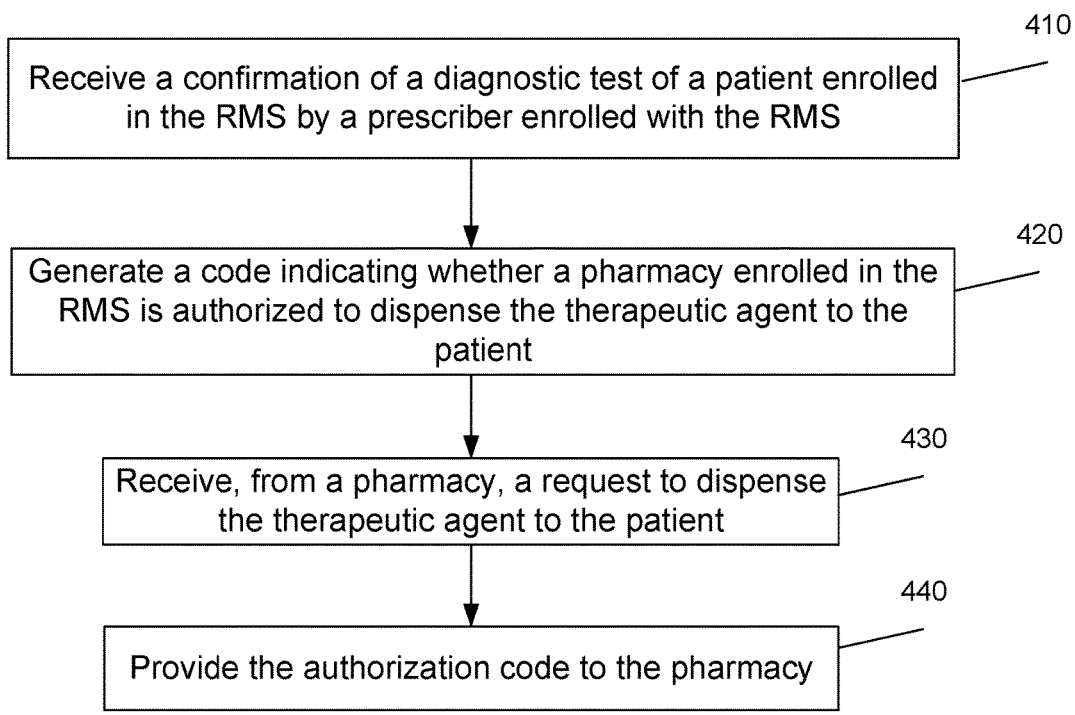
FIG. 4 is a flow chart illustrating a method of the RMS host device of FIG. 1, according to an embodiment.

Explained with reference to FIG. 1, FIG. 4 illustrates a method 400 of authorizing a pharmacy (e.g., the dispenser 116) to dispense a therapeutic agent associated with at least one indication to a patient, such as the patient 114, according to an embodiment. In some embodiments, the therapeutic agent is tolvaptan. In some embodiments, the at least one indication includes hyponatremia. In some embodiments, the at least one indication includes autosomal dominant polycystic kidney disease (ADPKD). In some embodiments, the therapeutic agent is associated with multiple indications.

At 410, a confirmation of a diagnostic test of a patient enrolled in the RMS is received at the host device 100 by the prescriber 112, where the prescriber is already enrolled with the RMS. At 420, based on the receipt of the confirmation from the prescriber 112, an authorization code is generated that indicates whether the pharmacy enrolled in the RMS is authorized to dispense the therapeutic agent to the patient 114. At 430, a request is received, from the pharmacy, to dispense the therapeutic agent to the patient 114, and at 440, the authorization code is provided to the pharmacy.

In some embodiments, the confirmation includes an identifier of a date on which the diagnostic test was performed on the patient, and the code is generated if the request is received within a predetermined time period from the date. In some embodiments, the confirmation includes an identifier of a date on which the diagnostic test was performed on the patient, and the code is valid for a predetermined time period from the date.

In some embodiments, the method 400 further includes transmitting, from the host device 100 to the prescriber 114, a request for the confirmation of the diagnostic test. The confirmation can be received in response to the request for the confirmation. In some embodiments, the method 400 further includes verifying that at least one of the pharmacy or a pharmacist associated with the pharmacy is enrolled in the RMS prior to providing the authorization code. In some embodiments, the method 400 further includes verifying an enrollment status of the prescriber prior generating the code.

In some embodiments, the confirmation includes confirmation of a successful diagnostic test, and the authorization code authorizes the pharmacy to dispense the therapeutic agent to the patient. In some embodiments, the confirmation includes confirmation of an unsuccessful diagnostic test and/or an adverse event associated with the patient using the therapeutic agent, and the authorization code prohibits the pharmacy from dispensing the therapeutic agent to the patient. In some embodiments, the adverse event is associated with one or more side effects associated with the at least one indication. In other embodiments, the adverse event is associated with one or more side effects unrelated to the at least one indication.

Figure 5:
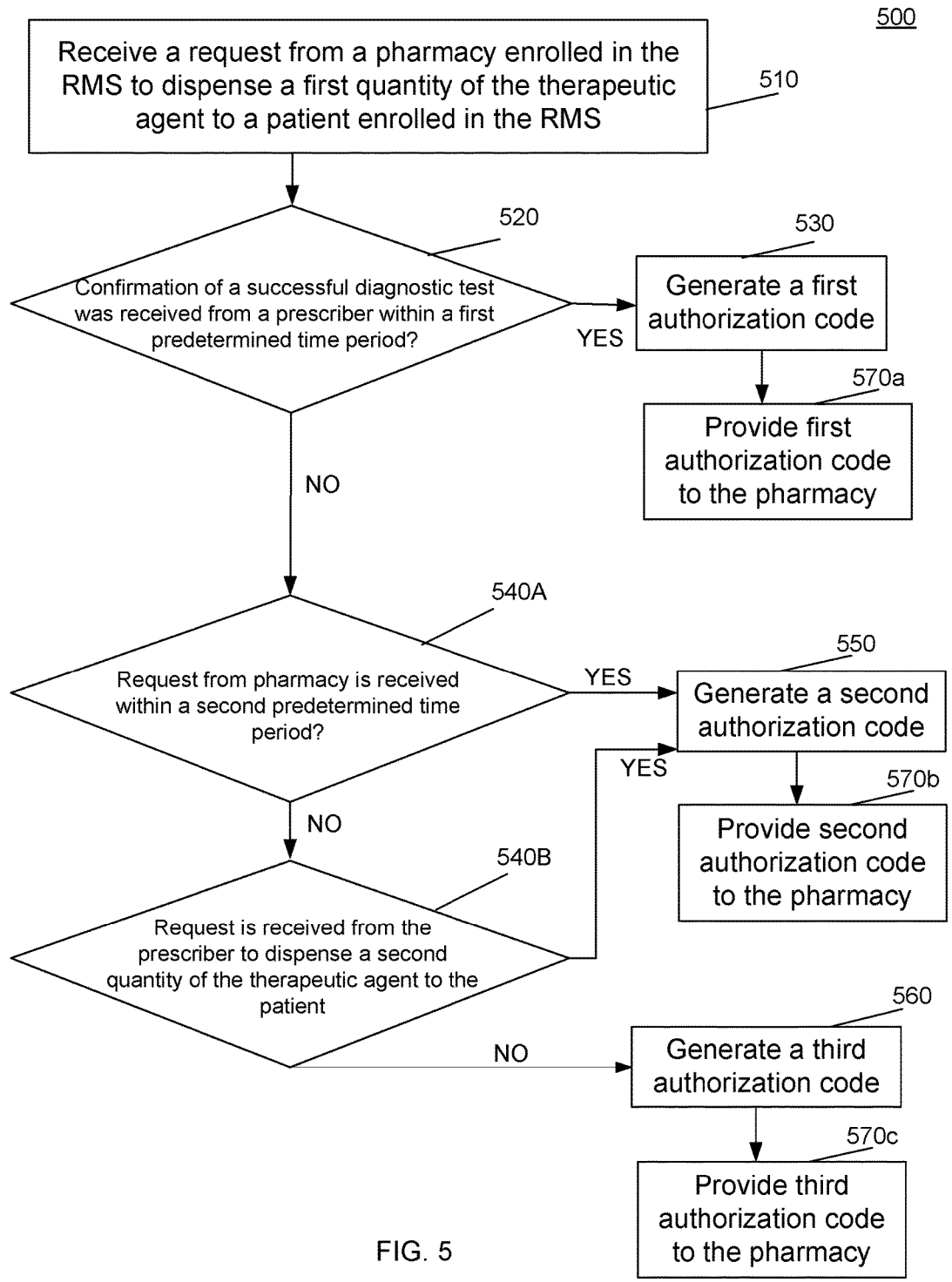
FIG. 5 is a flow chart illustrating a method of the RMS host device of FIG. 1, according to an embodiment.

Explained with reference to FIG. 1, FIG. 5 illustrates another method 500 of authorizing a pharmacy (e.g., the dispenser 116) to dispense a therapeutic agent associated with at least one indication to a patient, such as the patient 114, according to an embodiment. In some embodiments, the therapeutic agent is tolvaptan. In some embodiments, the at least one indication includes hyponatremia. In some embodiments, the at least one indication includes autosomal dominant polycystic kidney disease (ADPKD). In some embodiments, the therapeutic agent is associated with multiple indications.

At 510, a request is received at the RMS host device 100 from the pharmacy already enrolled with the host device, to dispense a first quantity (e.g., a prescribed and/or standard quantity) of the therapeutic agent to a patient already enrolled with the host device (e.g., by the dispenser module 128).

At 520, the host device 100 determines if a confirmation of a successful diagnostic test of the patient has been received from a prescriber (e.g., the prescriber 112) within a first predetermined time period such as can be received by the prescriber module 124, for example). If the confirmation is received, a first authorization code is generated at 530, and the generated first authorization code is transmitted to the pharmacy at 570*a*. In some embodiments, the first authorization code permits the pharmacy to dispense a first quantity of therapeutic agent to the patient.

If the confirmation is not received (as determined at step 520), then at 540A, the host device 100 determines if the request from the pharmacy is received within a second predetermined time period. If this is the case, then a second authorization code is generated at 550 (e.g., by the authorization module 130), and the generated second authorization code is transmitted to the pharmacy at 570*b*.

If the request from the pharmacy is not received within a second predetermined time period (as determined at step 540A), then at 540B, the host device 100 determines if a request is received from the prescriber (e.g., a dispense request, as described earlier) to dispense a second quantity of the therapeutic agent to the patient. If this is the case, then the second authorization code is generated at 550 (e.g., by the authorization module 130), and the generated second authorization code is transmitted to the pharmacy at 570*c*. If this is not the case, then a third authorization code is generated at 560, and the generated third authorization code is transmitted to the pharmacy at 580. In some embodiments, the second authorization code permits the pharmacy to dispense a second quantity of the therapeutic agent to the patient without the confirmation of a successful diagnostic test. In some embodiments, the second quantity is less than the first quantity. In some embodiments, the third authorization code prohibits the pharmacy from dispensing the therapeutic agent to the patient.

It is understood that while FIG. 5 illustrates that step 540A is performed before step 540B, in other embodiments, steps 540A and 540B can be performed substantially in parallel, and in yet other embodiments, step 540B can be performed before 540A. Irrespective of the order in which steps 540A and 540B are performed, it is further understood that (as is also the case in the illustrated embodiment of FIG. 5) the second authorization code is generated if either step 540A or step 540B is found to be true, and that the third authorization code is generated if both step 540A and step 540B are found to be false. In yet other embodiments, one of step 540A or step 540B is performed, the second authorization code is generated if the performed step is found to be true, and the third authorization code is generated if the performed step is found to be false.

In yet other embodiments, steps 540A and 540B are performed sequentially or substantially in parallel, the second authorization code is generated if both steps 540A, 540B are found to be true, and the third authorization code is generated if either of the steps 540A, 540B are found to be false. In this manner, the patient receives the second quantity of the therapeutic agent if the prescriber sends in the dispensing request and the pharmacy makes an authorization request within the second predetermined time period, and not otherwise.

Figure 6:
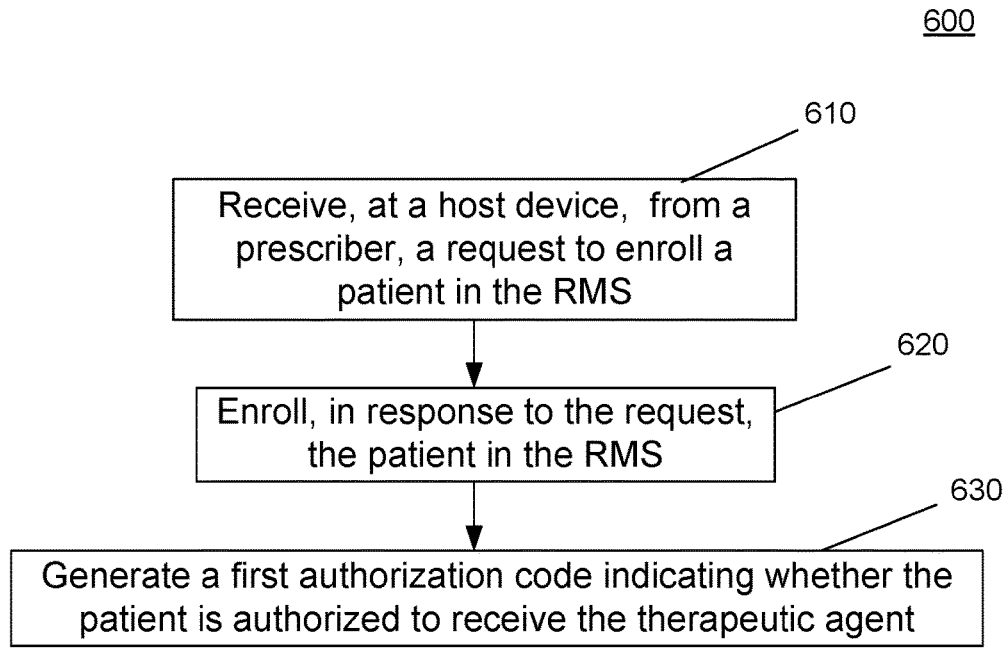
FIG. 6 is a flow chart illustrating a method of the RMS host device of FIG. 1, according to an embodiment.

Explained with reference to FIG. 1, FIG. 6 illustrates a method 600 of whether a patient, such as the patient 114, is authorized to receive a therapeutic agent for a first indication of multiple indications associated with the therapeutic agent, according to an embodiment. In some embodiments, the therapeutic agent is tolvaptan. In some embodiments, the indications include hyponatremia. In some embodiments, the indications includes autosomal dominant polycystic kidney disease (ADPKD).

At 610, a request is received, at a host device of a RMS (e.g., by the patient module 126 and/or the prescriber module 124) for a therapeutic agent associated with a multiple indications, from a prescriber, a request to enroll a patient in the RMS. In some embodiments, the request includes a specification of an indication from the multiple indications, such as a first indication or a second indication, and a confirmation of a diagnostic test conducted on a patient. The diagnostic test can be associated with the therapeutic agent and with the specified indication. At 620, the patient is enrolled in the RMS at the host device and in response to the request (e.g., by the patient module 126). In some embodiments, enrolling the patient includes identifying a predetermined enrollment period based on the indication. The predetermined enrollment period can have a first duration when the indication is a first indication from the multiple indications. The predetermined enrollment period can have a second duration different from the first duration when the indication is a second indication from the multiple indications. Hence, in some embodiments, at least two indications, such as the first indication and the second indication, are associated with different durations of enrollment. In other embodiments, each indication can be associated with a different duration of enrollment. At 630, a first authorization code is generated based on the predetermined enrollment period (e.g., by the authorization module 130). The first authorization code can indicate whether the patient is authorized to receive the therapeutic agent.

In some embodiments, the method 600 further includes receiving a request from a pharmacy to dispense a refill of the therapeutic agent to the patient. The method 600 can additionally include generating a new authorization code indicating whether the patient is authorized to receive a refill of the therapeutic agent. In some embodiments, generating the new authorization code for the first indication is different from generating the new authorization code for the second indication. Similarly stated, a different approach, algorithm, process, and/or the like can be employed depending on the indication for which the patient is receiving the therapeutic agent. In some embodiments, the same approach, algorithm, process, and/or the like can be used for generating the new authorization code for two or more indications.

In some embodiments, the confirmation of the diagnostic test is a first confirmation. In some embodiments, when the indication is the first indication, the method 600 can include generating the new authorization code in response to receiving, at the host device and from the prescriber, a confirmation of a second diagnostic test within the predetermined enrollment period. For example, if the patient is enrolled for a year and the patient is required to undergo testing every month to obtain a monthly refill of the therapeutic agent, the first duration can be about a month, or less than a month. The second diagnostic test can be related to, for example, a refill request or a reenrollment request. In some embodiments, when the indication is the second indication, the method 600 can include generating the new authorization code in response to receiving a request within the predetermined enrollment period and without receiving the confirmation of the second diagnostic test. For example, if the patient is enrolled for a month, then the second duration can be a month and the second confirmation is properly received anytime within the second duration without requiring confirmation of a subsequent diagnostic test.

In some embodiments, the method 600 further includes providing, after the enrolling and to the prescriber, prior to lapse of the first predetermined enrollment period, patient reenrollment information associated with: (1) the RMS, (2) the therapeutic agent, and (3) the first indication. In some embodiments, the method 600 additionally includes receiving consent from the prescriber and the patient in response to the patient reenrollment information, and reenrolling, at the host device, the patient in the RMS in response to receiving the consent.

In some embodiments, the method 600 further includes receiving, at the host device, for the therapeutic agent, from a prescriber, a request to enroll the prescriber in the RMS. The method 600 can additionally include providing, to the prescriber, educational material associated with the RMS, the therapeutic agent and/or the indication. The method 600 can also include providing, to the prescriber, access to a test relating to the educational material, and receiving, at the host device, an identifier of a performance of the prescriber on the test. The method 600 can further include enrolling, at the host device, the prescriber in the RMS if the performance of the prescriber meets a performance criterion for the test.

In some embodiments, the method 600 further includes receiving, at the host device, for the therapeutic agent, from a pharmacy, a request to enroll the pharmacy in the RMS. The method 600 can additionally include providing, to a pharmacist associated with the pharmacy, educational material associated with the RMS, the therapeutic agent and/or the indication. The method 600 can further include providing, to the pharmacist, access to a test relating to the educational material, and receiving, at the host device, an identifier of a performance of the pharmacist on the test. The method 600 can also include enrolling, at the host device, the pharmacy in the RMS if the performance of the pharmacist meets a performance criterion for the test.

FIGS. 7A-7E are illustrations of interactions between the various entities of FIG. 1 in the scenario in which the RMS device 100 is a REMS host that is compliant with the FDA's REMS requirement, according to an embodiment. FIGS. 7A-7E illustrate a RMS Host 700 (similar to the host device 100), a prescriber 712 (similar to the prescriber 112), a patient 714 (similar to the patient 114), and a pharmacy 716 (similar to the dispenser 116).

Figure 7A:
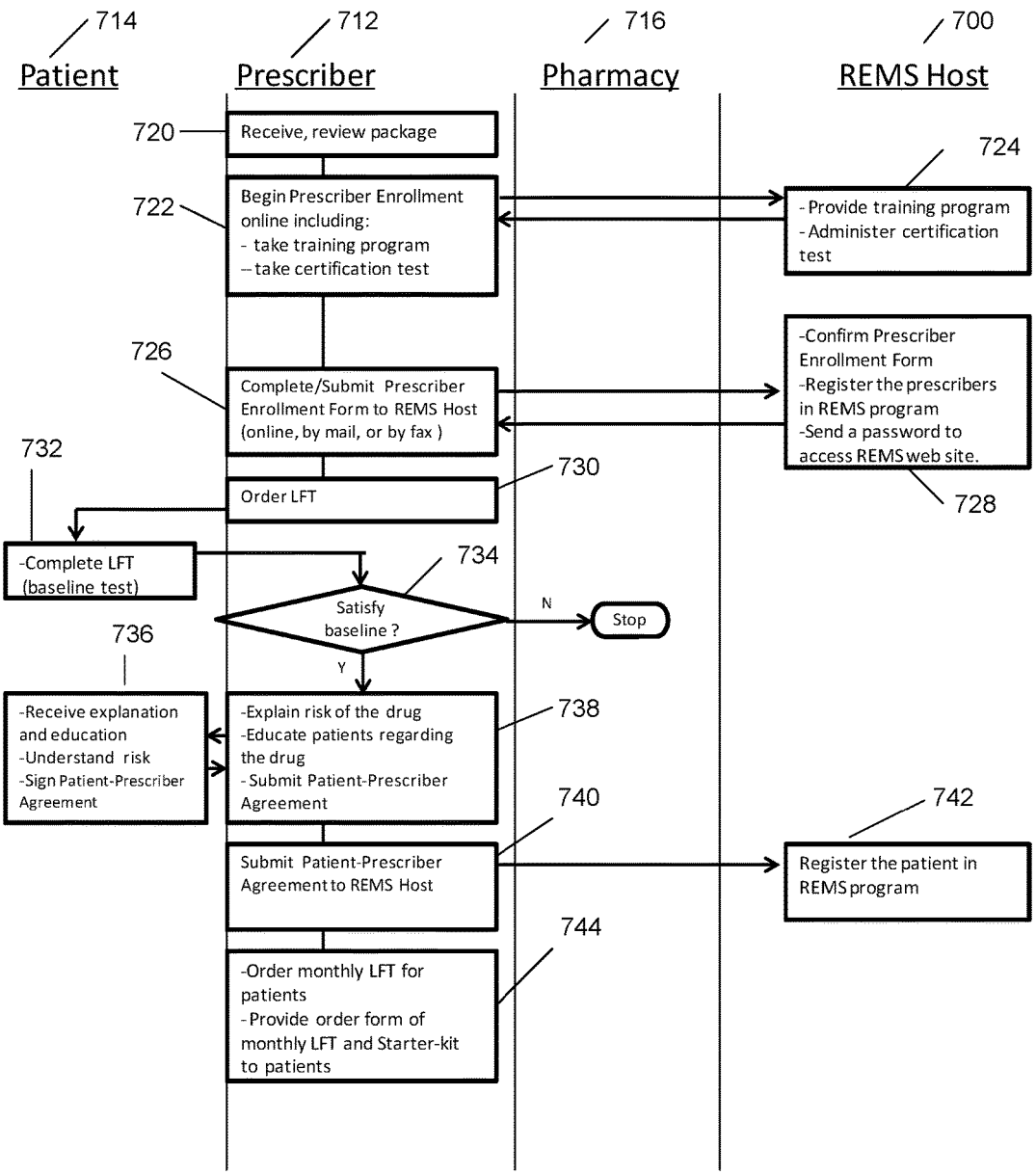
FIGS. 7A-7E are examples of information flow between the various entities illustrated in FIG. 1.

FIG. 7A is an illustration of prescriber enrollment and patient enrollment, according to an embodiment. At 720, the prescriber 712 receives a package containing educational information and certification information, inviting the prescriber 712 to enroll in a REMS program at the REMS host 700. At 722, the prescriber 712 uses the package information to contact the REMS Host 700 to obtain the training program and to subsequently take the prescriber certification test, which are provided/administered by the REMS host 700 at 724 (or a third-party). Assuming the prescriber 712 meets performance criterion for the certification test, at 726, the prescriber completes and submits a prescriber enrollment form to the REMS Host 700 via any suitable means such as email, online via a web interface, via fax, and/or the like. The REMS Host 700, at 728, confirms receipt of the prescriber enrollment form and registers the prescriber 712 in the REMS program (e.g., generates and saves a prescriber profile in a database). The REMS Host 700 also sends the prescriber 712 a password for future access to the REMS program/web site.

After enrolling, the prescriber 712 can prescribe the therapeutic agent pursuant to conditions agreed upon during prescriber enrollment. Accordingly, when the prescriber 712 determines, during counseling the patient 714, that the patient should receive the therapeutic agent or drug, the prescriber orders a liver function test (LFT) for the patient at 730. The patient 714 undergoes the test at 732, and at 734, the prescriber 712 determines whether the LFT satisfies specific baseline parameters for markers such as total bilirubin, alanine aminotransferase, aspartate aminotransferase and/or the like. If the baseline parameters are not satisfied, no further action is taken. If the baseline parameters are satisfied, the prescriber 712 can counsel the patient 714 at 738, including explaining the risks of the drug, educate the patient about the drug and the need for periodic LFT, and submitting a patient prescriber agreement form (similar to a patient enrollment form) to the patient 714 at 736. The patient 714 in turn, receives the counseling/education, and signs the patient-prescriber agreement form at 736. At 740, the prescriber 712 submits the signed patient-prescriber agreement to the REMS Host 700, which in turn registers the patient 714 in the REMS program. The prescriber 712 can subsequently order monthly LFTs for the patient 714 at 744, at which point the prescriber can provide the patient the LFT order forms for his convenience/records, and a helpful starter kit for the drug, including directions for use, the importance of monthly testing, and/or the like.

Figure 7B:
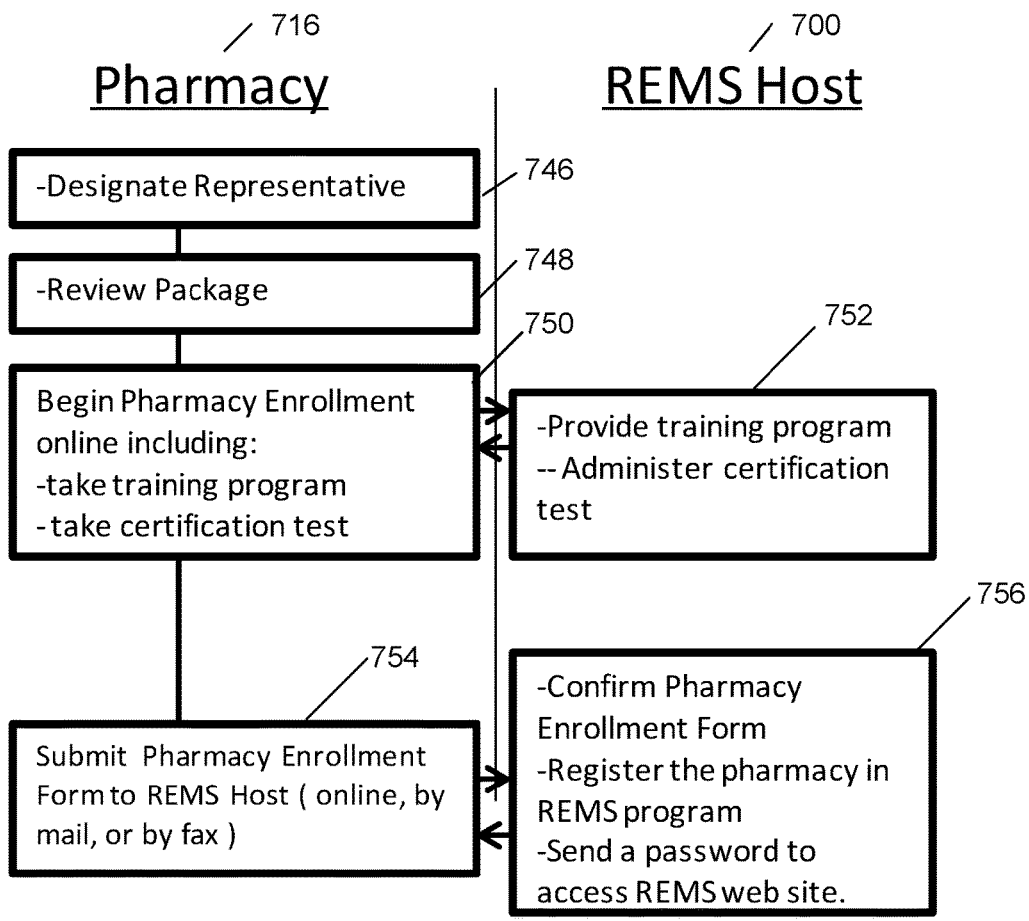

FIG. 7B is an illustration of pharmacy enrollment, according to an embodiment. At 746, the pharmacy 716 can designate (at 746) a representative to undergo the training/certification program for enrollment in the REMS program hosted by the REMS Host 700. At 748, the representative reviews enrollment information in a received package. At 750, the representative accesses the training program on the REMS Host 700 and takes the certification test. At 752, the REMS host 700 provides the training program and administers the prescriber certification test. If the representative's performance meets a performance criterion for the prescriber certification test, then at 754, the representative or another pharmacy member submits the pharmacy enrollment form (similar to a prescriber enrollment form) to the REMS Host 700, which in turn (among other things) registers the pharmacy 716 with the REMS program.

Figure 7C:
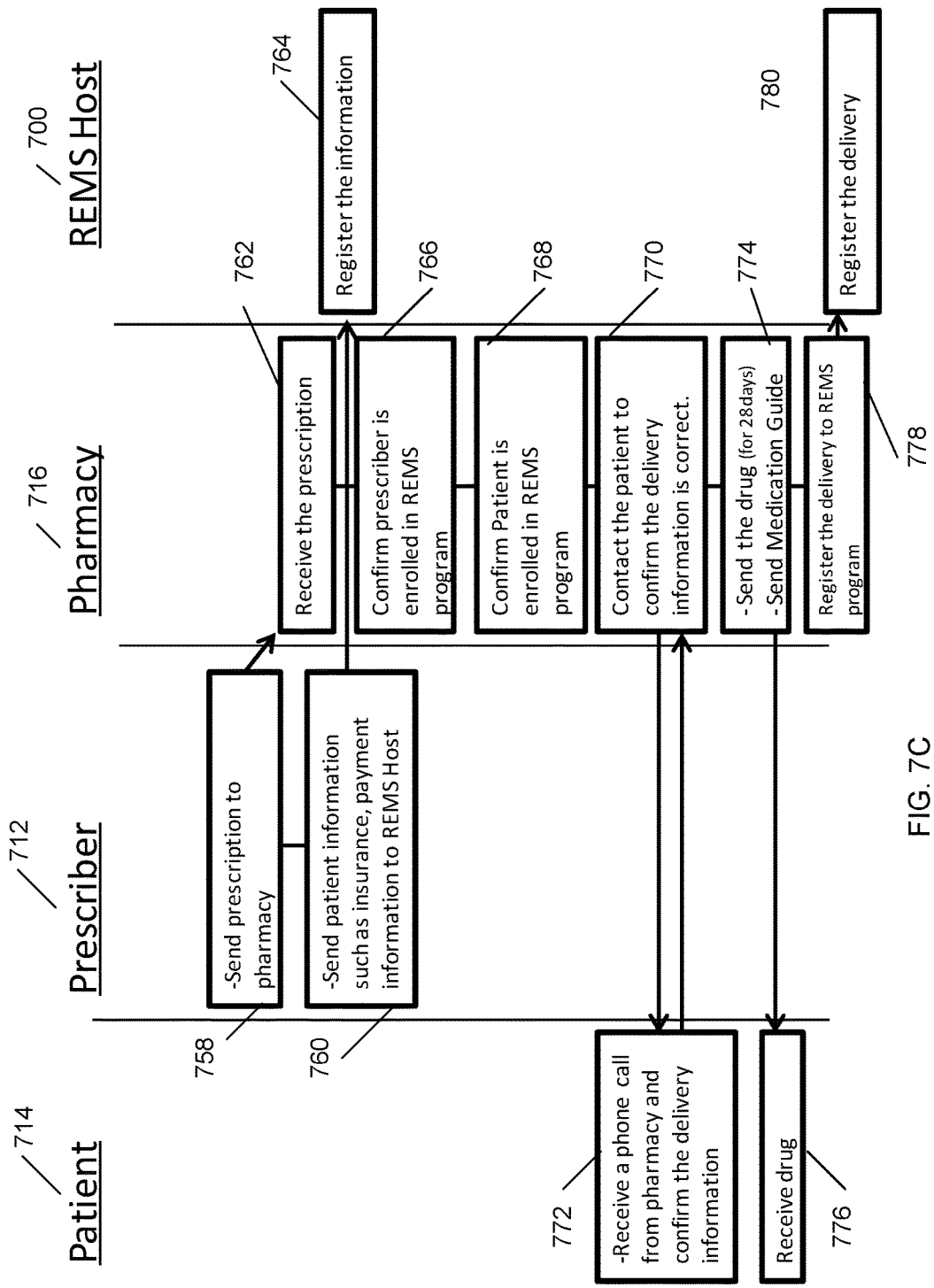

FIG. 7C is an illustration of dispensing a first prescription for the patient 714, according to an embodiment. At 758, the prescriber 712 sends a prescription for the therapeutic agent/drug to the pharmacy 716, either as part of the patient-prescriber agreement form or separately. The prescriber 712 can also (see step 760) send other patient information, such as insurance information, to the REMS Host 700. The REMS Host 700 can register the received information by, for example, associating the information with a patient profile of the patient 714. The pharmacy confirms, prior to dispensing the drug based on the prescriber, whether the prescriber is enrolled in the REMS program (see step 766) and whether the patient is enrolled in the REMS program (see step 768). The pharmacy 716 can then contact the patient 712 to confirm delivery option (e.g., a mailing address of the patient) at 772. The patient confirms delivery information at 772, in response to which the pharmacy 716 delivers the drug to the patient at 774, who receives it at 776. The pharmacy 716 also transmits the delivery information to the REMS program at 778, and the REMS Host registers the delivery at 780 by, for example, associating the delivery with the patient profile of the patient 714.

Figure 7D:
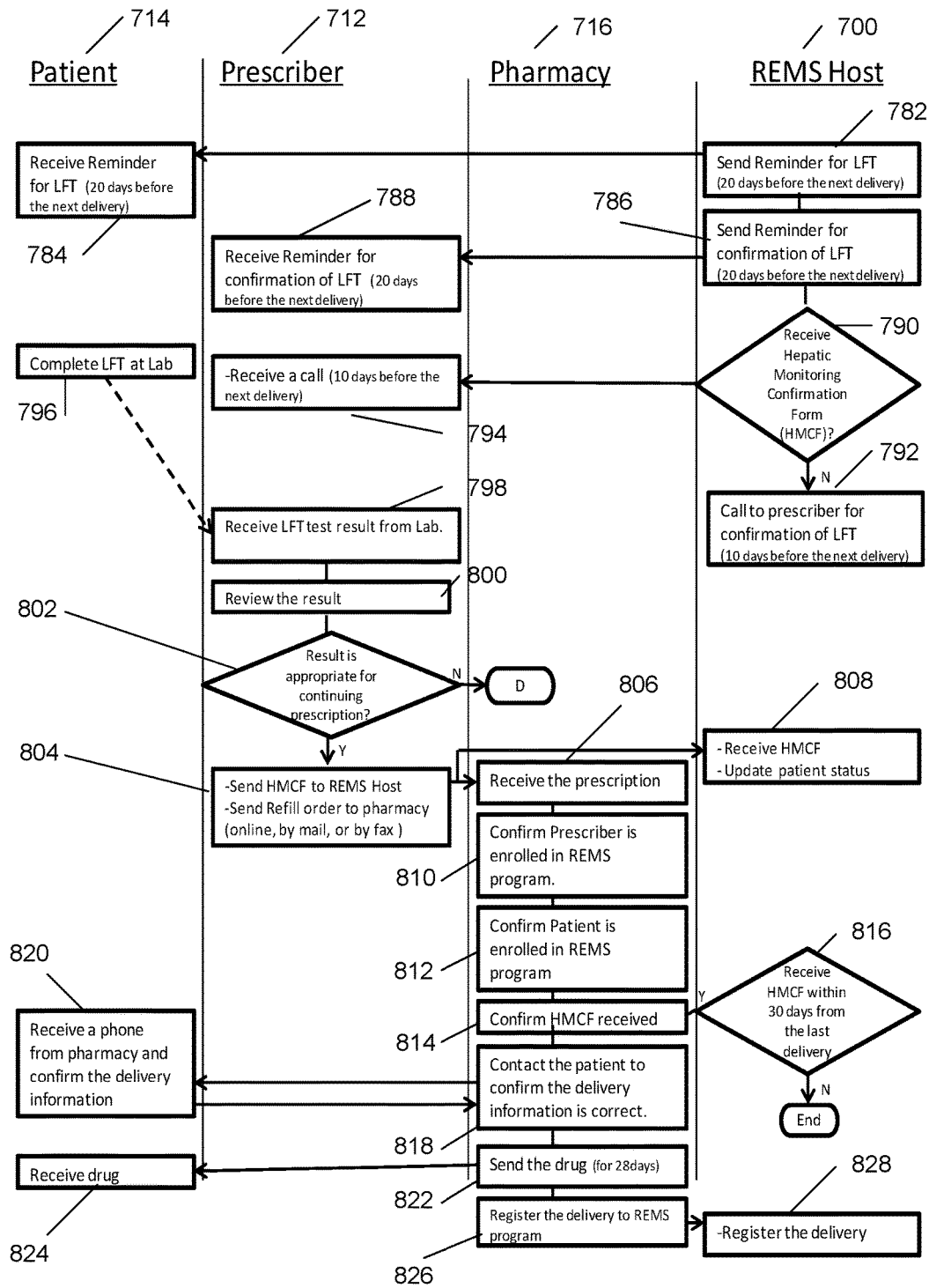

FIG. 7D is an illustration of dispensing a subsequent prescription (e.g., a refill) for the patient, according to an embodiment. Assuming the patient receives a refill every 28 days during enrollment, at 782, the REMS Host 700, not having received confirmation of a LFT, sends a reminder to the patient 714 for the LFT at 782 (the patient receives the reminder at 784), and a reminder to the prescriber 712 for the confirmation of the LFT at 786 (the prescriber receives the reminder at 788), both reminders sent and received 20 days before the next refill date. At 790, approximately 10 days before the next refill date, the REMS Host 700 determined whether a test confirmation form (here, a hepatic monitoring confirmation form, or HMCF) is received. If not, a phone call reminder is placed to the prescriber 712 at 792, and is received by the prescriber at 794.

At some point, the patient 714 completes the LFT at 796, and the LFT results are received (step 798) and reviewed (step 800) by the prescriber 712. If the prescriber 712 deems the LFT results to be unsuitable for continued prescription of the therapeutic agent, the prescriber reports the unfavorable results at D (described in more detail in FIG. 7E). If the prescriber 712 deems he LFT results to be suitable, the prescriber can order a refill for the patient 714, as well as send the HMCF to the REMS Host 700. The pharmacy 716 receives the refill prescription at 806, and the REMS Host 700 receives the HMCF at 808, and can update the patient status (e.g., the patient profile) based on the HMCF.

The pharmacy 716 confirms prescriber enrollment (step 810) and patient enrollment (step 812). The pharmacy 716 also ensures, by contacting the REMS Host 700, that a HMCF was received, at 814. Steps 810, 812, 814 can generally encompass an authorization request from the pharmacy 716 to the REMS Host 700 prior to dispensing the drug, as discussed earlier, and the response(s) received therefrom. The REMS Host 700 checks at 816 to ensure at least one HMCF associated with the patient profile was received within 30 days from the last time the therapeutic agent was dispensed. If this is not the case, no further action is take by the REMS Host 700 or the pharmacy 716. If the condition at 816 is satisfied, the pharmacy 716 can proceed to dispense the drug in a manner similar to described above, include confirming delivery operation at 818 (the patient 714 confirms at 820) and sending the drug at 822 (the patient receives the drug at 824). The pharmacy 716 also transmits delivery information to the REMS Host 700 at 826, and the REMS Host registers the delivery information at 828.

Figure 7E:
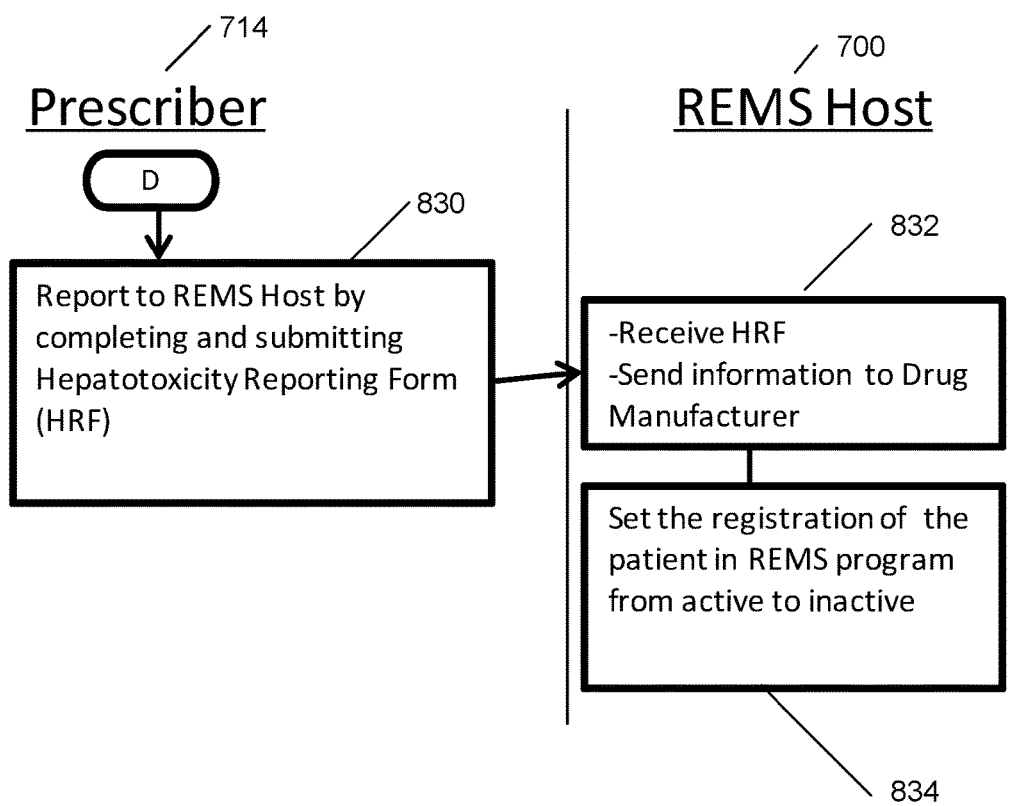

FIG. 7E is an illustration of the prescriber 714 reporting unfavorable LFT reports, according to an embodiment. At 830, the prescriber 814 completes a hepatotoxicity reporting form (HRF), such as can be provided to the REMS Host via a web interface, email, fax, and/or the like. At 832, the REMS Host 700 receives the HRF and, in this embodiment, shares the HRF with, for example, the manufacturer of the drug. At 834, the REMS Host 700 further ensures the patient does not receive additional quantities of the drug by changing the status of the patient to inactive, thereby effectively 'un-enrolling' the patient 714.

Figure 8:
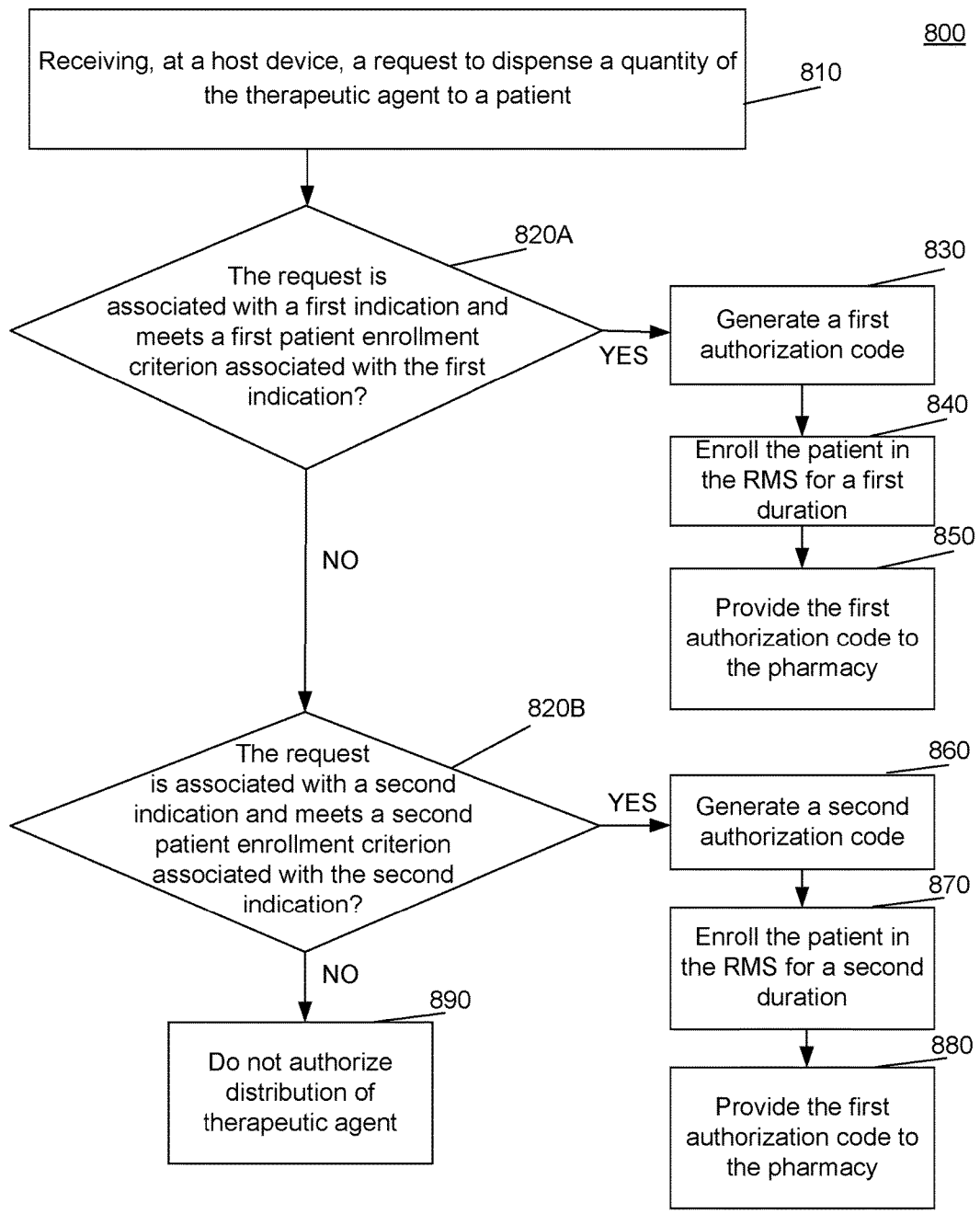
FIG. 8 is a flow chart illustrating a method of the RMS host device of FIG. 1, according to an embodiment.

Explained with reference to FIG. 1, FIG. 8 illustrates a method 800 of authorizing a patient, such as the patient 114, to receive a therapeutic agent associated with multiple indications, if the patient meets certain enrollment criteria. In some embodiments, the patient can be enrolling in RMS for the first time. In other embodiments, the patient can be reenrolling in the RMS and/or obtaining a refill of the therapeutic agent. In some embodiments, the therapeutic agent is tolvaptan. In some embodiments, the indications include hyponatremia. In some embodiments, the indications includes autosomal dominant polycystic kidney disease (ADPKD).

At 810, a request to dispense a quantity of the therapeutic agent to a patient is received from a compute device associated with a pharmacy enrolled in the RMS, such as the dispenser 116. In some embodiments, the request can include a specification and/or identifier of an indication from the multiple indications. In other embodiments, the request can include an identifier associated with the indication and/or patient and the RMS can identify the indication based on analyzing a profile of the patient in the RMS and identified by the identifier associated with the indication and/or patient.

At 820A, it is determined (e.g., by the patient module 126) if the indication is a first indication from the multiple indications and if the request meets a patient enrollment criterion associated with the first indication. If this is found to be the case, a first authorization code is generated at 830 (e.g., by the authorization module 130), and the patient is enrolled (or reenrolled) in the RMS for a first duration at 840. The enrollment criterion can be any suitable requirement(s) that the request must/should meet for patient enrollment including, but not limited to, that the request specify diagnostic test results related to the therapeutic agent (e.g., to monitor the potential for and/or the actual occurrence of adverse side effects), that the request include requested patient identification information, that the request identify the first indication, and/or the like. At 850, the first authorization code is provided to the pharmacy, such as by, for example, the authorization module 130 (e.g., sent to a compute device of the pharmacy via a network, telephonically, and/or the like).

In some embodiments, the first indication is autosomal dominant polycystic kidney disease (ADPKD), and the patient enrollment criterion associated with the first indication includes confirmation of a diagnostic test, and further includes an indication of diagnosis of ADPKD. In some embodiments, the diagnostic test can be a liver function test (LFT).

Substantially simultaneously, before, or after step 820A, at 820B, it is determined (e.g., by the patient module 126) if the indication is a second indication from the multiple indications and the request meets a patient enrollment criterion associated with the second indication. If this is found to be the case, a second authorization code is generated at 860, and the patient is enrolled (or reenrolled) in the RMS for a second duration at 870. In some embodiments, the second indication is hyponatremia, and the second patient enrollment criterion includes at least one of: an indication of diagnosis of hyponatremia; a date of hospitalization of the patient; a date of initiation of treatment with the therapeutic agent (e.g., in a hospital setting); a name and location associated with the site of treatment (e.g., a name and address of an hospital where the patient is being treated); an indication of a daily dose of the treatment with the therapeutic agent; or an indication of the patient's serum sodium concentration. At 880, the first authorization code or the second authorization code is provided to the pharmacy, such as by, for example, the authorization module 130 (e.g., sent to a compute device of the pharmacy via a network, telephonically, and/or the like). In some embodiments, if the conditions of step 820A are satisfied, then step 820B is not executed, and vice versa, i.e., if step 820B are satisfied, then step 820A is not executed.

In other embodiments, instead of performing steps 820A and 820B, the RMS identifies the indication for which the request is associated after step 810. If the request is associated with the first indication, the RMS determines whether the request meets a first patient enrollment criterion, and if so, proceeds to step 830. If the request is associated with the second indication, the RMS determines whether the request meets a second patient enrollment criterion, and if so, proceeds to step 860. In such an embodiment, the RMS identifies the indication prior to analyzing the enrollment criterion. In such embodiments, the enrollment criterion for the identified indication is analyzed, but the enrollment criterion for the non-identified indication is not analyzed.

In some embodiments, at step 890, if the request does not meet the patient enrollment criterion for either indication, the patient is not enrolled (or reenrolled), and the pharmacy is not authorized to dispense the therapeutic agent to the patient. This can be communicated to the pharmacy and/or patient in any suitable manner including, for example, not responding to the request, generating a code indicative of the request not meeting the dispensation criterion, and/or the like. In some embodiments, the first indication is autosomal dominant polycystic kidney disease (ADPKD) and the second indication is hyponatremia. In other embodiments, the first indication and/or the second indication can be any other suitable indications associated with a therapeutic agent.

Figure 9:
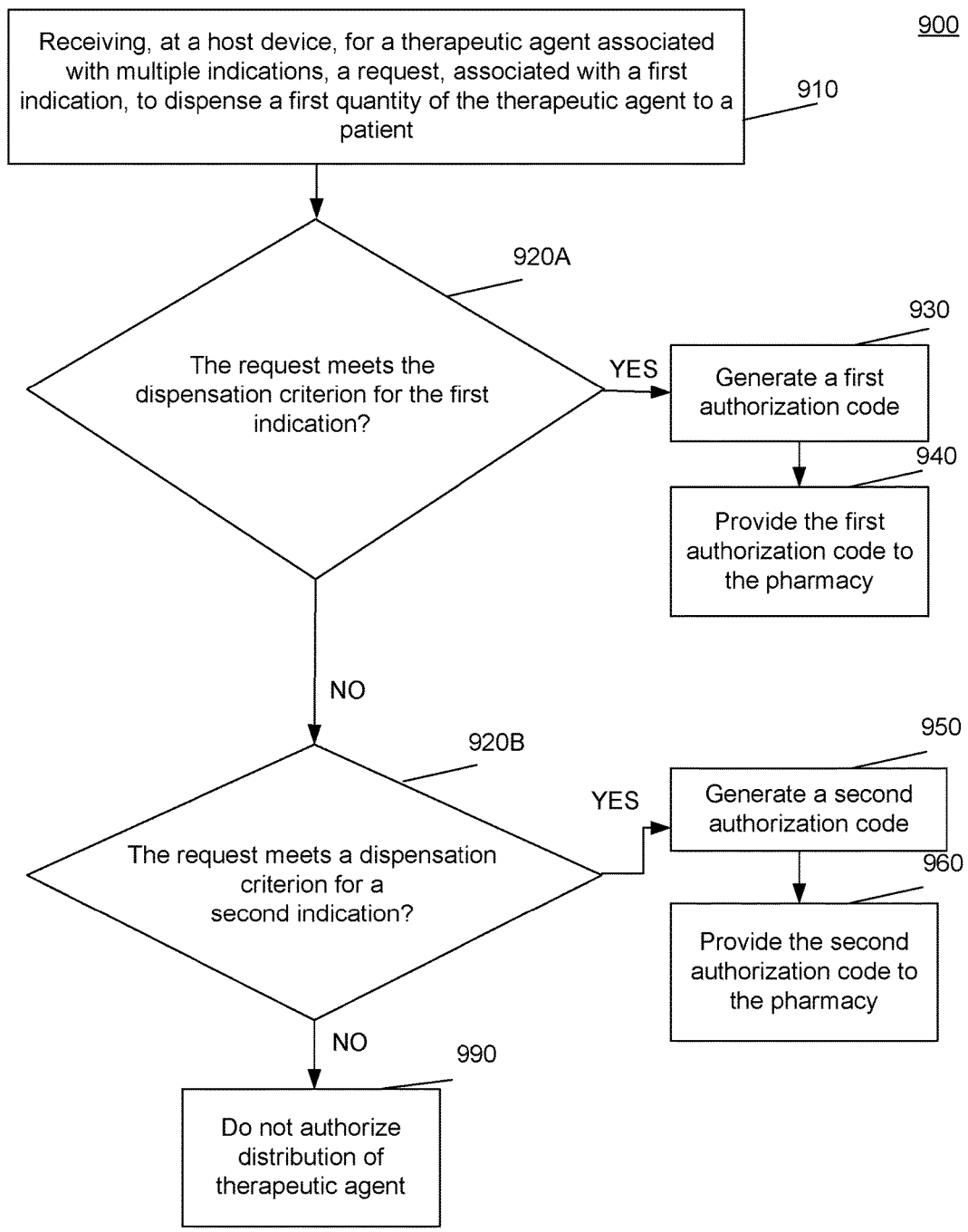
FIG. 9 is a flow chart illustrating a method of the RMS host device of FIG. 1, according to an embodiment.

Explained with reference to FIG. 1, FIG. 9 illustrates a method 900 of authorizing a patient, such as the patient 114, to receive a therapeutic agent associated with of the patient's indication, if certain dispensation criteria associated with either the patient's indication, or another indication associated with the therapeutic agent are met. In some embodiments, the patient can be enrolling in RMS for the first time. In other embodiments, the patient can be reenrolling in the RMS and/or obtaining a refill of the therapeutic agent. For example, method 900 can be used for a patient already enrolled in the RMS, but needing a refill of the therapeutic agent. In some embodiments, the therapeutic agent is tolvaptan. In some embodiments, the multiple indications include hyponatremia. In some embodiments, the multiple indications includes autosomal dominant polycystic kidney disease (ADPKD). In other embodiments, the therapeutic agent can be any other suitable therapeutic agent and/or a first indication and/or a second indication can be any other suitable indications associated with that therapeutic agent.

At 910, a request is received (e.g., by the dispenser module 128) from a compute device associated with a pharmacy (e.g., the dispenser 116) enrolled in the RMS to dispense the therapeutic agent to a patient. In some embodiments, the request includes an identifier of a first indication associated with the therapeutic agent. In other embodiments, the request can include an identifier associated with the patient and the RMS can identify the first indication based on analyzing a profile of the patient in the RMS and identified by the identifier associated with the patient.

At 920A, it is determined if the request meets the dispensation criterion for the first indication. If this is found to be the case, a first authorization code is generated at 930. At 940, the first authorization code is provided to the dispenser 116 (e.g., sent to a compute device of the pharmacy via a network, telephonically, and/or the like), such that the pharmacy/dispenser can use the authorization code to dispense the therapeutic agent to the patient.

If the request does not meet the dispensation criterion for the first indication at 920A, at 920B, it is determined (e.g., by the authorization module 130) if the request meets a dispensation criterion associated with a second indication. If this is found to be the case, a second authorization code is generated at 950. At 960, the second authorization code is provided to the dispenser 116 (e.g., sent to a compute device of the pharmacy via a network, telephonically, and/or the like), such that the pharmacy/dispenser can use the authorization code to dispense the therapeutic agent to the patient for the first indication. In some embodiments, at 990, if the request does not meet the dispensation criterion associated with a second indication at 920B, the pharmacy is not authorized to dispense the therapeutic agent to the patient. This can be communicated to the pharmacy and/or patient in any suitable manner including, for example, not responding to the request, generating a code indicative of the request not meeting the dispensation criterion, and/or the like. In some embodiments, if the conditions of step 920A are satisfied, then step 920B and its subsequent steps are not executed, and vice versa, i.e., if the conditions of step 920B are satisfied, then step 920A and its subsequent steps are not executed.

In some embodiments, the dispensation criterion associated with the second indication includes a confirmation of a diagnostic test conducted on the patient and associated with the therapeutic agent. In some embodiments, for example, the diagnostic test is an LFT. In some embodiments, for example, the first indication is hyponatremia and the second indication is autosomal dominant polycystic kidney disease (ADPKD). The dispensation criterion can include any suitable requirement(s) that the request must satisfy to authorize the patient to receive the therapeutic agent including, but not limited to, whether the patient has undergone a diagnostic test, whether the request is for an amount/number of doses/dosage strength that is appropriate for the patient's indication, and/or the like. In this manner, a therapeutic agent can be dispensed for a first indication if the requirement for dispensing the drug for a second indication are met. In some embodiments, the dispensation criterion for the second indication can be greater/more stringent than that for the first indication, and places a greater demand on the patient if he/she wishes to acquire the therapeutic agent in the instance of not meeting the dispensation criterion for his/her indication.

Figure 10:
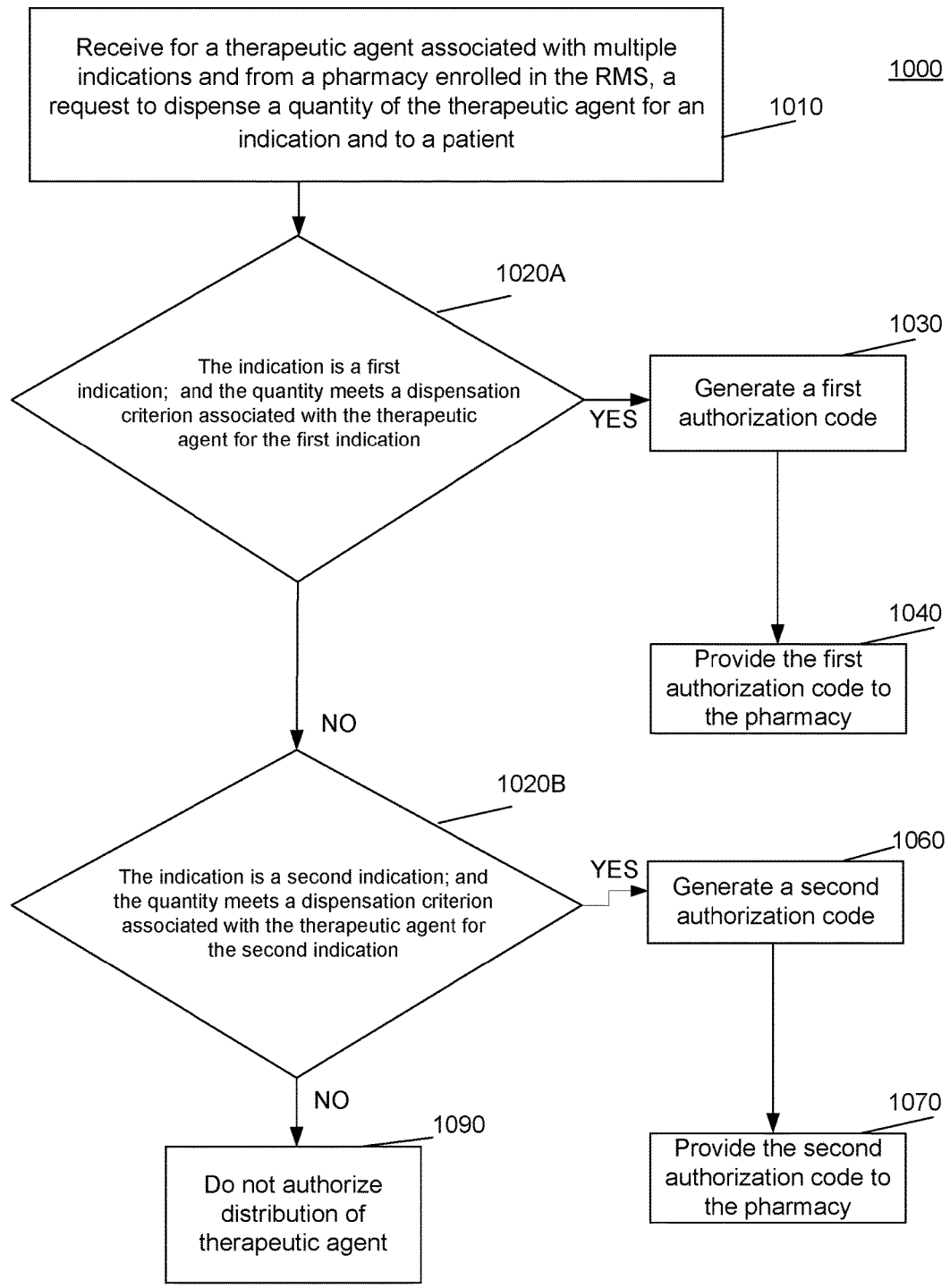
FIG. 10 is a flow chart illustrating a method of the RMS host device of FIG. 1, according to an embodiment.

Explained with reference to FIG. 1, FIG. 10 illustrates a method 1000 of authorizing a patient, such as the patient 114, to receive a therapeutic agent for an indication, if certain dispensation criteria and/or enrollment criteria are met for that indication. In some embodiments, the patient can be enrolling in RMS for the first time. In other embodiments, the patient can be reenrolling in the RMS and/or obtaining a refill of the therapeutic agent. In some embodiments, the therapeutic agent is tolvaptan. In some embodiments, the indication is one of multiple indications associated with the therapeutic agent. In some embodiments, the multiple indications includes hyponatremia. In some embodiments, the multiple indications includes autosomal dominant polycystic kidney disease (ADPKD).

At 1010, a request to dispense a quantity of the therapeutic agent to a patient is received (e.g., by the dispenser module 128) from a compute device associated with a pharmacy enrolled in the RMS (e.g., the dispenser 116). The request can include a specification and/or identifier associated with an indication from the multiple indications. The request can also include an indication of the quantity/form of therapeutic agent to dispense (e.g., the dosage, whether in tablet/capsule/liquid form, number of units, etc.). In other embodiments, the request can include an identifier associated with the patient and the RMS can identify the indication and/or the quantity/form of the therapeutic agent based on analyzing a profile of the patient in the RMS and identified by the identifier associated with the patient.

At 1020A, it is determined (e.g., by the RMS device 100) if (1) the indication in the request is a first indication from the multiple indications, and (2) the quantity meets a dispensation criterion associated with the therapeutic agent for the first indication. If this is found to be the case, a first authorization code is generated at 1030. At 1040, the first authorization code is provided to the compute device associated with the pharmacy (e.g., sent to a compute device of the pharmacy via a network, telephonically, and/or the like).

In some embodiments, the first indication is hyponatremia, and the dispensation criterion associated with the first indication includes at least one of: an indication of diagnosis of hyponatremia; a date of hospitalization of the patient; a date of initiation of treatment with the therapeutic agent; a daily dose of the treatment with the therapeutic agent; or an indication of the patient's serum sodium concentration. In some embodiments, the first indication is hyponatremia, the therapeutic agent is Tolvaptan, and the dispensation criterion associated with the therapeutic agent for the first indication can be, for example, between 15 mg daily to 60 mg daily. For example, the dispensation criterion can be from about 15 mg daily, about 20 mg daily, about 30 mg daily, about 40 mg daily, about 50 mg daily, about 55 mg daily, and/or about 60 mg daily, including values and/or sub-ranges in-between. In other embodiments, the dispensation criterion associated with the first indication can be any other suitable dose, such as, for example, less than 15 mg daily or greater than 60 mg daily. In some embodiments, the dispensation criterion associated with the therapeutic agent for the first indication can be, for example, between 5 mg doses to 45 mg doses. For example, the dispensation criterion for the first indication can be based on about 5 mg doses of the therapeutic agent, about 10 mg doses, about 15 mg doses, about 20 mg doses, about 25 mg doses, about 30 mg doses, about 35 mg doses, about 40 mg doses, and/or about 45 mg doses, combinations thereof, and/or values in between. In other embodiments, the dispensation criterion associated with the first indication can be any other suitable dose amount, such as, for example, less than 5 mg doses or greater than 45 mg doses.

If the conditions of step 1020A are not met, at 1020B, it is determined if (1) the indication in the request is a second indication from the multiple indications, and (2) (3) the quantity meets a dispensation criterion associated with the therapeutic agent for the second indication. If this is found to be the case, a second authorization code is generated at 1060. In some embodiments, if the conditions of step 1020A are satisfied, then step 1020B and its subsequent steps are not executed, and vice versa, i.e., if the conditions of step 1020B are satisfied, then step 1020A and its subsequent steps are not executed.

In some embodiments, at 1090, if the request does not meet the criterion of 1020A or 1020B, t the pharmacy is not authorized to dispense the therapeutic agent to the patient. This can be communicated to the pharmacy and/or patient in any suitable manner including, for example, not responding to the request, generating a code indicative of the request not meeting the dispensation criterion, and/or the like.

In some embodiments (not shown), step 1020A can further includes the determination whether the request meets a patient enrollment criterion associated with the first indication; if this is the case, and if other aspects of step 1020A are also satisfied, the patient can be enrolled in the RMS for a first duration associated with the first indication.

In some embodiments (not shown), step 1020B can further includes the determination whether the request meets a patient enrollment criterion associated with the second indication; if this is the case, and if other aspects of step 1020B are also satisfied, the patient can be enrolled in the RMS for a second duration (which can be different than the first indication) associated with the second indication.

In some embodiments, the second indication is autosomal dominant polycystic kidney disease (ADPKD), and the dispensation criterion associated with the second indication includes an indication of diagnosis of ADPKD, and a confirmation of a diagnostic test conducted on the patient and associated with the therapeutic agent. In some embodiments, the diagnostic test is a LFT. In some embodiments, the second indication is autosomal dominant polycystic kidney disease (ADPKD), the therapeutic agent is Tolvaptan, and the dispensation criterion associated with the therapeutic agent for the second indication can be, for example, between a 15 mg dose to a 120 mg dose. For example, the dispensation criterion can be a 15 mg dose, a 20 mg dose, a 30 mg dose, a 40 mg dose, a 50 mg dose, a 60 mg dose, a 70 mg dose, a 80 mg dose, a 90 mg dose, a 100 mg dose, and/or a 120 mg dose, combinations thereof, including all sub values. In other embodiments, the dose can be any other suitable dose, for example, below 15 mg or above 120 mg. At 1070, the second authorization code is provided to the compute device associated with the pharmacy (e.g., sent to a compute device of the pharmacy via a network, telephonically, and/or the like).

In some embodiments, if (1) the indication is a first indication from the multiple indications, (2) the quantity does not meets a dispensation criterion associated with the therapeutic agent for the first indication, and (3) the quantity meets a dispensation criterion associated with the therapeutic agent for the second indication, the method 1000 can further include generating a warning code, such as, for example, at step 1090. In this manner, the pharmacy/dispenser can be warned that the patient is requesting a quantity presribable for a different indication.

While various embodiments have been described herein, it should be understood that they have been presented by way of example, and not limitation. Where methods described above indicate certain events occurring in certain order, the ordering of certain events may be modified. Additionally, certain of the events may be performed concurrently in a parallel process when possible, as well as performed sequentially as described herein.

Although some of the modules are described as providing interfaces for interacting with the prescriber 112, the patient 114, the dispenser 116, and/or other users of the RMS host device 100, it is understood that in some embodiments, some or all such interactions may be enabled via an integrated portal usable by each of these entities. In such embodiments, each entity interacting with the portal can have an account and/or be otherwise registered with the host device 100. In some embodiments, the registration can be linked and/or included in profile information of the entity. For example, the registration of the prescriber 112 can be linked to the prescriber profile for that particular prescriber. As another example, the registration of a pharmacy (i.e., a dispenser) and/or one or more pharmacists for the pharmacy can be linked to the dispenser profile for the pharmacy.

Although not described in detail here, the host device 100 can include additional modules and/or functionality for interacting with other entities such as insurance providers, diagnostic testing laboratories, distribution vendors, and/or the like. For example, an insurance provider can require confirmation of a successful diagnostic test before reimbursing the patient and/or the dispenser for the therapeutic agent. As another example, the prescriber can directly order diagnostic tests for the patient at the diagnostic testing laboratory via the host device 100. As yet another example, a distribution vendor responsible for delivering the therapeutic agent to a vendor can check if the vendor is enrolled at the host device 100, can receive notifications whenever a dispenser is enrolled/un-enrolled at the host device, and/or the like.

Although the prescription for the therapeutic agent is described as being provided by the prescriber to the patient, in other embodiments, the prescription information is additionally or alternatively included in the patient enrollment form by the prescriber. In such embodiments, the host device 100 can perform additional checks to ensure the patient is receiving the prescribed dose. For example, in the embodiment of FIG. 5, the first or second authorization code would only be generated if the host device determines the patient has not exhausted his prescription. If the prescription permitted five refills, the patient would be unable to obtain a sixth refill even if a successful diagnostic test had been confirmed in a timely manner by the prescriber (e.g., within the first predetermined time period), since the host device would generate the third authorization code, forbidding the pharmacy from dispensing the therapeutic agent to the patient. While a trained pharmacist and state of the art pharmacy systems would typically catch such an oversight, such aspects of the host device 100 can provide an additional layer of security against oversight and/or potential abuse.

In some embodiments, the patient visits the dispenser for the first time the therapeutic agent is dispensed to the patient, and the prescribed refills can be provided to the patient thereafter by the dispenser without any further action on the patient's part. For example, the dispenser can, prior to when the patient is expected to run out of the last dispensed quantity of the therapeutic agent, submit an authorization request to the host device 100 as described earlier. In this manner, the dispenser can verify the patient is authorized to continue receiving the therapeutic agent, and mail the refill of the therapeutic agent to the patient in a timely manner.

In some embodiments, a method includes receiving, at a host device of a risk management system (RMS) for a therapeutic agent associated with at least one indication, from a prescriber, a request to enroll the prescriber in the RMS. The method also includes providing, to the prescriber, educational material associated with the RMS and associated with the therapeutic agent. The method further includes providing, to the prescriber, access to a test relating to the educational material, and receiving, at the host device, an identifier of a performance of the prescriber on the test. The method also includes enrolling, at the host device, the prescriber in the RMS if the performance of the prescriber meets a performance criterion for the test.

In some embodiments, the therapeutic agent is tolvaptan. In some embodiments, the at least one indication includes hyponatremia. In some embodiments, the at least one indication includes autosomal dominant polycystic kidney disease (ADPKD). In some embodiments, the enrolling includes authorizing the prescriber to prescribe the therapeutic agent.

In some embodiments, enrolling the prescriber can include enrolling the prescriber for a predetermined time period. In some embodiments, the method can further include providing, after the enrolling and to the prescriber, prior to lapse of the predetermined time period, reenrollment information associated with the RMS and with the therapeutic agent. The method can also include receiving consent from the prescriber in response to the reenrollment information, and reenrolling, at the host device, the prescriber in the RMS in response to receiving the consent.

In some embodiments, the therapeutic agent is associated with multiple indications.

In some embodiments, another method includes receiving, at a host device of a risk management system (RMS) for a therapeutic agent associated with at least one indication, from a pharmacy, a request to enroll the pharmacy in the RMS. The method also includes providing, to a pharmacist associated with the pharmacy, educational material associated with the RMS and with the therapeutic agent. The method also includes providing, to the pharmacist, access to a test relating to the educational material. The method further includes receiving, at the host device, an identifier of a performance of the pharmacist on the test. The method also includes enrolling, at the host device, the pharmacy in the RMS if the performance of the pharmacist meets a performance criterion for the test.

In some embodiments, the therapeutic agent includes tolvaptan. In some embodiments, the at least one indication includes hyponatremia. In some embodiments, the at least one indication includes autosomal dominant polycystic kidney disease (ADPKD). In some embodiments, the enrolling includes authorizing the pharmacy to dispense the therapeutic agent.

In some embodiments, the enrolling includes enrolling the pharmacy for a predetermined time period. In some embodiments, the method can further include providing, after the enrolling and to the pharmacist prior to lapse of the predetermined time period, reenrollment information associated with the RMS and with the therapeutic agent. The method can also include receiving consent from the pharmacist in response to the reenrollment information, and reenrolling, at the host device, the pharmacist in the RMS in response to receiving the consent.

In some embodiments, another method includes receiving, at a host device of a risk management system (RMS) for a therapeutic agent associated with at least one indication, a confirmation of a diagnostic test of a patient enrolled in the RMS by a prescriber enrolled with the RMS. The method also includes, based on the receipt of the confirmation from the prescriber, generating a code indicating whether a pharmacy enrolled in the RMS is authorized to dispense the therapeutic agent to the patient. The method also includes receiving, at the host device and from a compute device associated with the pharmacy, a request to dispense the therapeutic agent to the patient. The method also includes providing the authorization code to the compute device associated with the pharmacy.

In some embodiments, the confirmation includes an identifier of a date on which the diagnostic test was performed on the patient. In some embodiments, generating the code includes generating the code if the request is received within a predetermined time period from the date.

In some embodiments, the method can further include transmitting, from the host device to the prescriber, a request for the confirmation of the diagnostic test. The confirmation can be received in response to the request for the confirmation.

In some embodiments, the therapeutic agent includes tolvaptan. In some embodiments, the at least one indication includes hyponatremia. In some embodiments, the at least one indication includes autosomal dominant polycystic kidney disease (ADPKD).

In some embodiments, the method can further include verifying that at least one of the pharmacy or a pharmacist associated with the pharmacy is enrolled in the RMS prior to providing the authorization code. In some embodiments, the confirmation can include confirmation of a successful diagnostic test. In such embodiments, the code authorizes the pharmacy to dispense the therapeutic agent to the patient.

In some embodiments, the method can further include re-enrolling the patient in the RMS based on the successful diagnostic test.

In some embodiments, the confirmation includes confirmation of at least one of an unsuccessful diagnostic test or an adverse event associated with the patient using the therapeutic agent. In such embodiments, the authorization code prohibits the pharmacy from dispensing the therapeutic agent to the patient. In some embodiments, the adverse event is associated with one or more side effects associated with the at least one indication. In some embodiments, the method can further include verifying an enrollment status of the prescriber prior to the generating.

In some embodiments, another method includes receiving, at a host device of a risk management system (RMS) for a therapeutic agent associated with at least one indication, a request from a pharmacy enrolled in the RMS to dispense a first quantity of the therapeutic agent to a patient enrolled in the RMS. The method further includes generating a first authorization code if a confirmation of a successful diagnostic test of the patient was received from a prescriber enrolled in the RMS within a first predetermined time period. The method also includes generating a second authorization code if: the confirmation of the successful diagnostic test of the patient was not received within the first predetermined time period, and the request from the compute device associated with the pharmacy is received within a second predetermined time period; or a request is received from a compute device associated with the prescriber to dispense a second quantity of the therapeutic agent to the patient, the second quantity different from the first quantity; or both. The method also includes generating a third authorization code if the confirmation of the successful diagnostic test of the patient was not received within the first predetermined time period and if the request from the compute device associated with the prescriber to dispense the second quantity of the therapeutic agent is not received. The method also includes providing the first authorization code, the second authorization code, or the third authorization code to the compute device associated with the pharmacy.

In some embodiments, the therapeutic agent includes tolvaptan. In some embodiments, the at least one indication includes hyponatremia. In some embodiments, the at least one indication includes autosomal dominant polycystic kidney disease (ADPKD).

In some embodiments, the first authorization code authorizes the pharmacy to dispense the first quantity of the therapeutic agent to the patient, the first quantity being a standard quantity. In some embodiments, the second authorization code authorizes the pharmacy to dispense the second quantity of the therapeutic agent to the patient without the confirmation of the successful diagnostic test. In some embodiments, the third authorization code prohibits the pharmacy from dispensing the therapeutic agent to the patient.

In some embodiments, the method can further include transmitting, from the host device to the prescriber, a request for the confirmation of the successful diagnostic test. In such embodiments, the confirmation is received in response to the request for the confirmation.

In some embodiments, another method includes receiving, at a host device of a risk management system (RMS) for a therapeutic agent associated with multiple indications, from a prescriber, a request to enroll a patient in the RMS. The request includes a specification of at least one indication, and a confirmation of a diagnostic test conducted on the patient. The diagnostic test is associated with the therapeutic agent and is associated with the a indication. The method can also include enrolling, at the host device, in response to the request, the patient in the RMS. Enrolling the patient includes identifying a predetermined enrollment period based on the indication. The predetermined enrollment period has a first duration when the indication is a first indication, and has a second duration different from the first duration when the indication is a second indication. The enrolling also includes, based on the predetermined enrollment period, generating an authorization code indicating whether the patient is authorized to receive the therapeutic agent.

In some embodiments, the method can further include receiving a request to dispense a refill of the therapeutic agent to the patient. The method can also include generating a new authorization code indicating whether the patient is authorized to receive a refill of the therapeutic agent using (1) a first process if the at least one indication is the first indication or (2) a second process different from the first process if the at least one indication is the second indication.

In some embodiments, the diagnostic test is a first diagnostic test. In some embodiments, the at least one indication is the first indication, and the method can further include generating the new authorization code in response to receiving, at the host device and from the prescriber, a confirmation of a second diagnostic test within the predetermined enrollment period. In some embodiments, the at least one indication is the second indication, and the method can further include generating the new authorization code in response to receiving a request within the predetermined enrollment period and without receiving the confirmation of the second diagnostic test.

In some embodiments, the method can further include providing, after the enrolling and to the prescriber, prior to lapse of the predetermined enrollment period, patient reenrollment information associated with: (1) the RMS, (2) the therapeutic agent, and (3) the first indication. The method can also include receiving consent from the prescriber and the patient in response to the patient reenrollment information, and reenrolling, at the host device, the patient in the RMS in response to receiving the consent.

In some embodiments, the method can further include receiving, at the host device, for the therapeutic agent, from a prescriber, a request to enroll the prescriber in the RMS. The method can also include providing, to the prescriber, educational material associated with the RMS and associated with the therapeutic agent. The method can also include providing, to the prescriber, access to a test relating to the educational material, and receiving, at the host device, an identifier of a performance of the prescriber on the test. The method can also include enrolling, at the host device, the prescriber in the RMS if the performance of the prescriber meets a performance criterion for the test.

In some embodiments, the method can also include receiving, at the host device, for the therapeutic agent, from a pharmacy, a request to enroll the pharmacy in the RMS. The method can further include providing, to a pharmacist associated with the pharmacy, educational material associated with the RMS and with the therapeutic agent. The method can also include providing, to the pharmacist, access to a test relating to the educational material, and receiving, at the host device, an identifier of a performance of the pharmacist on the test. The method can also include enrolling, at the host device, the pharmacy in the RMS if the performance of the pharmacist meets a performance criterion for the test.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

While various embodiments have been described above, it should be understood that they have been presented by way of example, and not limitation. Where methods described above indicate certain events occurring in certain order, the ordering of certain events can be modified. Additionally, certain of the events may be performed concurrently in a parallel process when possible, as well as performed sequentially as described above.

What is claimed is:

1. A risk management system (RMS) device, comprising:
an RMS database; and
an RMS processor,
the RMS processor configured to receive, via a communication network and from a compute device associated with a prescriber, a request to enroll a patient in an RMS program of a therapeutic agent associated with a plurality of indications, the request including:
a specification of at least one indication from the plurality of indications; and
a confirmation of a diagnostic test conducted on the patient, the diagnostic test associated with the therapeutic agent and associated with the at least one indication from the plurality of indications,
the RMS processor further configured, in response to the request, to identify a predetermined enrollment period based on the at least one indication from the plurality of indications and to generate a patient profile, the patient profile including the predetermined enrollment period, the predetermined enrollment period having a first duration when the at least one indication is a first indication from the plurality of indications, the predetermined enrollment period having a second duration different from the first duration when the at least one indication is a second indication from the plurality of indications;
the RMS processor configured to store the patient profile in the RMS database;
the RMS processor configured to generate a first authorization code, based on the predetermined enrollment period, authorizing a pharmacy or the prescriber to dispense the therapeutic agent to the patient and to generate a plurality of additional authorization codes, each additional authorization code from the plurality of additional authorization codes including an initial default instruction prohibiting the pharmacy or the prescriber from dispensing the therapeutic agent, the RMS processor configured to associate the first authorization code and the plurality of additional authorization codes with the patient profile; and
the RMS processor configured to transmit via the communication network the first authorization code to at least one of a compute device associated with the pharmacy or the compute device associated with the prescriber such that the therapeutic agent can be dispensed to the patient based on the first authorization code, the RMS processor configured to transmit each additional authorization code from the plurality of additional authorization codes and including the initial default instruction via the communication network to at least one of the compute device associated with the pharmacy or the compute device associated with the prescriber such that the pharmacy or the prescriber is prohibited from dispensing the therapeutic agent based on the plurality of additional authorization codes for a time period after receiving each additional authorization code including the initial default instruction.

2. The RMS device of claim 1, wherein the RMS processor is further configured to:
receive, for the therapeutic agent, from the compute device associated with the pharmacy, a request to enroll the pharmacy in the RMS program;
transmit, to the compute device associated with the pharmacy, educational material associated with the RMS and the therapeutic agent;
transmit, to the compute device associated with the pharmacy, access to a test relating to the educational material for a user of the compute device associated with the pharmacy;
receive an identifier of a performance of the user of the compute device associated with the pharmacy on the test; and
generate a dispenser profile for the pharmacy if the identifier of the performance meets a performance criterion for the test,
the RMS processor further configured to store the dispenser profile in the RMS database as a new dispenser profile.

3. The RMS device of claim 1, wherein the RMS processor is further configured to:
generate, prior to lapse of the predetermined enrollment period, and after generating the patient profile, patient reenrollment information associated with: (1) the RMS program, (2) the therapeutic agent, and (3) the first indication;
transmit the patient reenrollment information to the compute device associated with the prescriber; and
receive an indication of consent from the compute device associated with the prescriber in response to the patient reenrollment information, the RMS processor further configured to update the patient profile in the RMS database in response to receiving the consent.

4. The RMS device of claim 1, wherein the RMS processor is configured to modify at least one additional authorization code from the plurality of additional authorization codes based on an event subsequent to the generation of the plurality of additional authorization codes such the at least one additional authorization code authorizes the pharmacy or the prescriber to dispense the therapeutic agent to the patient, the event including at least one of:
a receipt of a diagnostic test result,
a receipt of an adverse event report, or
a receipt of a dispensing request.

5. The method of claim 1, wherein the time period is a period of time between receipt of each additional authorization code including the initial default instruction and receipt of an additional authorization code that has been modified by the RMS processor such that the additional authorization code authorizes the pharmacy or the prescriber to dispense the therapeutic agent to the patient.

6. A risk management system (RMS) device, comprising:
a RMS database storing dispenser profiles, patient profiles, and prescriber profiles; and
a RMS processor,
the RMS processor configured to receive, for a therapeutic agent associated with a plurality of indications, a request from a compute device associated with a pharmacy to dispense a first quantity of the therapeutic agent to a patient, the RMS database including a dispenser profile for the pharmacy, the RMS database including a patient profile for the patient;
the RMS processor configured to receive a confirmation of a successful diagnostic test of the patient from a compute device associated with a prescriber, the RMS database including a prescriber profile for the prescriber;
the RMS processor configured to generate a first authorization code if the successful diagnostic test of the patient is associated with at least one indication from the plurality of indications and the confirmation of the successful diagnostic test of the patient was received within a first predetermined time period,
the RMS processor further configured to generate a second authorization code if at least one of: (1) the successful diagnostic test of the patient is associated with the at least one indication, the confirmation of the successful diagnostic test of the patient was not received within the first predetermined time period, and the request from the compute device associated with the pharmacy is received within a second predetermined time period, or (2) a request is received from the compute device associated with the prescriber to dispense a second quantity of the therapeutic agent to the patient, the second quantity different from the first quantity,
the RMS processor further configured to generate a third authorization code if: (1) the confirmation of the successful diagnostic test of the patient is not associated with the at least one indication or the confirmation of the successful diagnostic test of the patient was not received within the first predetermined time period, or (2) the request from the compute device associated with the prescriber to dispense the second quantity of the therapeutic agent is not received within a third predetermined time period; and
the RMS processor configured to transmit the first authorization code, the second authorization code, or the third authorization code to the compute device associated with the pharmacy such that the pharmacy is permitted to dispense the first quantity of the therapeutic agent if the compute device associated with the pharmacy receives the first authorization code, the pharmacy is permitted to dispense the second quantity of the therapeutic agent if the compute device associated with the pharmacy receives the second authorization code, and the pharmacy is prohibited from dispensing the first quantity and the second quantity if the compute device associated with the pharmacy receives the third authorization code.

7. The RMS device of claim 6, wherein the at least one indication includes at least one of hyponatremia or autosomal dominant polycystic kidney disease (ADPKD).

8. A method, comprising:
receiving, at a host device of a risk management system (RMS) for a therapeutic agent associated with a plurality of indications, from a compute device associated with a prescriber, a request to enroll the prescriber in the RMS;
enrolling, at the host device, the prescriber in the RMS if the performance of the prescriber meets a performance criterion for the test,
receiving, at the host device, from a compute device associated with the prescriber, a request to enroll a patient in the RMS, the request including a specification of at least one indication from the plurality of indications and a confirmation of a diagnostic test conducted on the patient, the diagnostic test associated with the therapeutic agent and associated with the at least one indication from the plurality of indications;
identifying, in response to receiving the request, a predetermined enrollment period based on the at least one indication from the plurality of indications, the predetermined enrollment period having a first duration when the at least one indication is a first indication from the plurality of indications, the predetermined enrollment period having a second duration different from the first duration when the at least one indication is a second indication from the plurality of indications;
generating a first authorization code based on the predetermined enrollment period authorizing a pharmacy or the prescriber to dispense the therapeutic agent to the patient;
generating a plurality of additional authorization codes, each additional authorization code from the plurality of authorization codes including an initial default instruction prohibiting the pharmacy or the prescriber from dispensing the therapeutic agent,
associating the first authorization code and the plurality of additional authorization codes with a patient profile; and
transmitting the first authorization code at least one of a compute device associated with the pharmacy or the compute device associated with the prescriber such that the therapeutic agent can be dispensed to the patient based on the first authorization code.

9. The method of claim 8, wherein the enrolling includes authorizing the prescriber to prescribe the therapeutic agent.

10. The method of claim 8, wherein the enrolling includes enrolling the prescriber for a predetermined time period, the method further comprising:

providing, after the enrolling and to the prescriber, prior to lapse of the predetermined time period, reenrollment information associated with the RMS and with the therapeutic agent;

receiving consent from the prescriber in response to the reenrollment information; and reenrolling, at the host device, the prescriber in the RMS in response to receiving the consent.

11. A method, comprising:

receiving, at a host device of a risk management system (RMS) for a therapeutic agent associated with a plurality of indications, a request from a compute device associated with a pharmacy enrolled in the RMS to dispense a first quantity of the therapeutic agent to a patient enrolled in the RMS, the request including a specification of at least one indication from the plurality of indications;

generating a first authorization code if a confirmation of a successful diagnostic test of the patient was received from a prescriber enrolled in the RMS within a first predetermined time period, the successful diagnostic test associated with the at least one indication from the plurality of indications, the first authorization code authorizing the pharmacy to dispense the first quantity of the therapeutic agent to the patient;

generating a second authorization code if at least one of: (1) the confirmation of the successful diagnostic test of the patient was not received within the first predetermined time period, and the request from the compute device associated with the pharmacy is received within a second predetermined time period; or (2) a request is received from a compute device associated with the prescriber to dispense a second quantity of the therapeutic agent to the patient, the second quantity different from the first quantity, the second authorization code authorizing the pharmacy to dispense the second quantity to the patient;

generating a third authorization code if the confirmation of the successful diagnostic test of the patient was not received within the first predetermined time period and if the request from the compute device associated with the prescriber to dispense the second quantity of the therapeutic agent is not received within a third predetermined time period, the third authorization code prohibiting the pharmacy from dispensing the therapeutic agent to the patient; and providing the first authorization code, the second authorization code, or the third authorization code to the compute device associated with the pharmacy.

12. The method of claim 11, wherein the first quantity is a standard quantity.

13. The method of claim 11, wherein the second authorization code authorizes the pharmacy to dispense the second quantity of the therapeutic agent to the patient without the confirmation of the successful diagnostic test.

14. The method of claim 11, further comprising transmitting, from the host device to the prescriber, a request for the confirmation of the successful diagnostic test, the confirmation received in response to the request for the confirmation.

15. The method of claim 11, further comprising:

receiving, at the host device of the RMS, the confirmation of the successful diagnostic test, the confirmation of the successful diagnostic test associated with a patient test result meeting a dispensation criterion for the at least one indication from the plurality of indications.

16. The method of claim 11, further comprising:

conducting a diagnostic test associated with the at least one indication from the plurality of indications to determine whether the diagnostic test is successful based on whether a patient test result meets a dispensation criterion for the at least one indication from the plurality of indications; and sending the confirmation of the successful diagnostic test of the patient to the host device of the RMS if the patient test result meets the dispensation criterion.

* * * * *